United States Patent
Ostadrahimi et al.

(10) Patent No.: US 10,716,488 B2
(45) Date of Patent: Jul. 21, 2020

(54) IMAGING USING GATED ELEMENTS

(71) Applicant: UNIVERSITY OF MANITOBA, Winnipeg (CA)

(72) Inventors: Majid Ostadrahimi, Winnipeg (CA); Joe Lovetri, Winnipeg (CA)

(73) Assignee: The University of Manitoba, Winnipeg (CA)

( * ) Notice: Subject to any disclaimer, the term of this patent is extended or adjusted under 35 U.S.C. 154(b) by 478 days.

(21) Appl. No.: 15/108,052

(22) PCT Filed: Dec. 29, 2014

(86) PCT No.: PCT/IB2014/067390
§ 371 (c)(1),
(2) Date: Jun. 24, 2016

(87) PCT Pub. No.: WO2015/101921
PCT Pub. Date: Jul. 9, 2015

(65) Prior Publication Data
US 2016/0317061 A1 Nov. 3, 2016

Related U.S. Application Data

(60) Provisional application No. 61/921,808, filed on Dec. 30, 2013.

(51) Int. Cl.
*A61B 5/05* (2006.01)
*G01S 13/89* (2006.01)
(Continued)

(52) U.S. Cl.
CPC ............ *A61B 5/0507* (2013.01); *G01N 22/00* (2013.01); *G01S 13/89* (2013.01); *A61B 2562/0228* (2013.01)

(58) Field of Classification Search
CPC .......... A61B 5/0507; A61B 2562/0228; G01N 22/00
See application file for complete search history.

(56) References Cited

U.S. PATENT DOCUMENTS 2,959,778 A * 11/1960 Bradley .................. G01S 7/034
333/103
3,659,293 A * 4/1972 Gupta .................. G01S 13/348
342/112

(Continued)

FOREIGN PATENT DOCUMENTS

EP 0 928 157 B1 7/1999
WO WO 2009/066186 A2 5/2009
(Continued)

OTHER PUBLICATIONS

M. Agnes et al., "Webster's New World College Dictionary," fourth edition; Wiley Publishing, Inc., Cleveland, Ohio, USA; copyright in the year 2007; ISBN 0-02-863119-6; entry for the word, "aperture," p. 65. (Year: 2007).*

(Continued)

*Primary Examiner* — Bernarr E Gregory
(74) *Attorney, Agent, or Firm* — Mueting Raasch Group

(57) ABSTRACT

Exemplary methods and systems may image an object of interest using one or more waveguide assemblies including gated elements. The gated elements may be configurable in a transmission state, a reception state, or a passive state. The exemplary methods and systems may deliver electromagnetic energy (e.g., microwave energy) to an object of interest using a gated element of a waveguide assembly configured in a transmission state and sample scattered field using a gated element of another waveguide assembly configured in the reception state while the remainder of gated elements are configured in the passive state.

45 Claims, 21 Drawing Sheets

(51) Int. Cl.
*G01N 22/00* (2006.01)
*G01S 13/00* (2006.01)

(56) References Cited

U.S. PATENT DOCUMENTS

| | | | | |
|---|---|---|---|---|
| 3,732,566 | A * | 5/1973 | Schubring | G01S 7/415 342/109 |
| 3,990,081 | A * | 11/1976 | Guennou | G01S 7/032 342/28 |
| 4,259,743 | A * | 3/1981 | Kaneko | G01S 7/032 333/247 |
| 4,319,244 | A * | 3/1982 | Hirota | G01S 7/032 342/104 |
| 4,344,440 | A * | 8/1982 | Aaby | A61B 5/05 324/642 |
| 5,051,748 | A | 9/1991 | Pichot et al. | |
| 5,227,800 | A * | 7/1993 | Huguenin | G01S 13/89 250/332 |
| 5,430,369 | A | 7/1995 | Blomey et al. | |
| 5,627,553 | A | 5/1997 | Poulton | |
| 5,704,355 | A | 1/1998 | Bridges | |
| 5,715,819 | A | 2/1998 | Svenson et al. | |
| 5,829,437 | A | 11/1998 | Bridges | |
| 5,999,836 | A | 12/1999 | Nelson et al. | |
| 6,061,589 | A | 5/2000 | Bridges et al. | |
| 6,275,045 | B1 | 8/2001 | Eloy | |
| 6,448,788 | B1 | 9/2002 | Meaney et al. | |
| 6,490,471 | B2 | 12/2002 | Svenson et al. | |
| 6,777,684 | B1 | 8/2004 | Volkov et al. | |
| 6,885,191 | B1 | 4/2005 | Gleman | |
| 6,965,340 | B1 | 11/2005 | Baharav et al. | |
| 7,167,133 | B2 | 1/2007 | Nagashima | |
| 7,439,736 | B2 | 10/2008 | Meaney et al. | |
| 7,746,266 | B2 | 6/2010 | Zoughi et al. | |
| 7,825,667 | B2 | 11/2010 | Fang et al. | |
| 7,843,347 | B2 | 11/2010 | Nikitin et al. | |
| 8,689,377 | B2 * | 4/2014 | Hannemann | A61B 5/05 324/309 |
| 8,724,864 | B2 | 5/2014 | Persson et al. | |
| 9,615,765 | B2 * | 4/2017 | Chayat | A61B 5/0507 |
| 2004/0077943 | A1 | 4/2004 | Meaney et al. | |
| 2005/0107692 | A1 | 5/2005 | Li et al. | |
| 2006/0239404 | A1 | 10/2006 | Upda et al. | |
| 2006/0293597 | A1 | 12/2006 | Johnson et al. | |
| 2007/0015993 | A1 | 1/2007 | Ciocan et al. | |
| 2011/0040176 | A1 | 2/2011 | Razansky | |
| 2011/0130656 | A1 * | 6/2011 | Son | A61B 5/0507 600/430 |
| 2011/0137381 | A1 | 6/2011 | Lee et al. | |
| 2011/0227586 | A1 | 9/2011 | Lovetri | |
| 2012/0330151 | A1 | 12/2012 | Weinstein et al. | |

FOREIGN PATENT DOCUMENTS

| | | |
|---|---|---|
| WO | WO 2009/066186 A3 | 7/2009 |
| WO | WO 2010/049253 A1 | 5/2010 |
| WO | WO 2013/005134 A2 | 1/2013 |

OTHER PUBLICATIONS

L. Jofre et al., "Medical Imaging with a Microwave Tomographic Scanner"; "IEEE Transactions on Biomedical Engineering"; vol. 37, No. 3; Mar. 1990; pp. 303-312; published by IEEE, Piscataway, New Jersey, USA. (Year: 1990).*

Abubakar et al., "2.5d forward and inverse modeling for interpreting low frequency electromagnetic measurements," Jul.-Aug. 2008, *Geophysics*, 73(4):F165-77.

Abubakar et al., "A multiplicative regularization approach for deblurring problems," Nov. 2004, *IEEE Transactions on Image Processing*, 13(11):1524-32.

Abubakar et al., "A robust iterative method for Born inversion," Feb. 2004, *IEEE Transactions on Geoscience and Remote Sensing*, 42(2):342-54.

Abubakar et al., "Imaging of biomedical data using a multiplicative regularized contrast source inversion method," *2002, IEEE Trans. Microw. Theory Tech.*, 50(7):1761-71.

Abubakar et al., "Iterative forward and inverse algorithms based on domain integral equations for three-dimensional electric and magnetic objects," 2004, *Journal of Computational Physics*, 195(1):236-62.

Abubakar et al., "Non-linear three-dimensional inversion of crosswell electrical measurements," 2000, *Geophysical Prospecting*, 48(1):109-34.

Abubakar et al., "The contrast source inversion method for location and shape reconstructions," 2002, *Inverse Problems*, 18:495-510.

Bolomey et al., *Engineering Applications of the Modulated Scatterer Technique*. Artech House, Inc.: Norwood, Massachusetts; 2001. Cover Page, Publisher's Page, and Table of Contents.

Bolomey et al., "On the possible use of microwave-active imaging for remote thermal sensing," Sep. 1983, *IEEE Transactions on Microwave Theory and Techniques*, 31(9):777-81.

Broquetas et al., "Cylindrical geometry: a further step in active microwave tomography," May 1991, *IEEE Transactions on Microwave Theory and Techniques*, 39(5):836-44.

Bulyshev et al., "Three-dimensional microwave tomography. Theory and computer experiments in scalar approximation," Jun. 2000, *Inverse Problems*, 16(3): 863-75.

Caorsi et al. "A passive antenna system for data acquisition in scattering applications". 2002. *IEEE Antennas and Wireless Propagation Letters*, 1:203-06.

Charbonnier et al., "Deterministic Edge-Preserving Regularization in Computed Imaging," Feb. 1997, *IEEE Transactions on Image Processing*, 6(2): 298-311.

Chew et al. "Reconstruction of two-dimensional permittivity distribution using the distorted born iterative method" Jun. 1990. *IEEE Transactions on Medical Imaging*, 9(2):218-25.

Crocco et al., "On embedded microwave imaging systems: retrievable information and design guidelines," Mar. 27, 2009, *Inverse Problems*, 25(6): 065001 (17 pgs).

Cullen et al. "A new perturbation method for measuring microwave fields in free space," Nov. 1955. *Proceedings of the IEE—Part B: Radio and Electronic Engineering*. 102(6):836-44.

De Zaeytijd et al. "Full-wave three-dimensional microwave imaging with a regularized Gauss-Newton method theory and experiment," Nov. 2007. *IEEE Transactions on Antennas and Propagation*, 55(11):3279-92.

Fang et al. "Viable three-dimensional medical microwave tomography: theory and numerical experiments," Feb. 1, 2010, *IEEE Transactions Antennas and Propagation*, 58(2):449-58.

Fear et al. "Microwave Detection of Breast Cancer," Nov. 2000, *IEEE Transactions on Microwave Theory and Techniques*, 48(11): 1854-63.

Fhager et al., "Reconstruction quality and spectral content of an electromagnetic time-domain inversion algorithm," Aug. 2006, *IEEE Transactions on Biomedical Engineering*, 53(8):1594-04.

Franchois et al., "Quantitative microwave imaging with a 2.45-GHz planar microwave camera," Aug. 1998, *IEEE Transactions on Medical Imaging*, 17(4): 550-61.

Franchois et al., "A quasi-Newton reconstruction algorithm for a complex microwave imaging scanner environment,"Jan. 10, 2003, *Radio Science*, 38(2): 8011-23.

Franza et al., "SICS: A sensor interaction compensation scheme for microwave imaging," Feb. 2002, *IEEE Transactions on Antennas and Propagation*, 50(2): 211-16.

Geffrin et al., "Continuing with the Fresnel database: experimental setup and improvements in 3D scattering measurements," 2009, *Inverse Problems*, 25:024001.

Ghasr et al. "A novel 24 GHz one-shot, rapid and portable microwave imaging system." (*IEEE Instrumentation and Measurement Technology Conference*) Victoria, Vancouver Island, Canada, May 12-15, 2008, 1798-1802.

Ghasr et al. "Portable real-time microwave camera at 24 GHz," Feb. 2012, *IEEE Transactions on Antennas and Propagation*, 60(2): 1114-25.

(56) References Cited

OTHER PUBLICATIONS

Gilmore et al., "A study of matching fluid loss in a biomedical microwave tomography system," Feb. 2013, *Medical Physics*, 40(2):023101.
Gilmore et al., "A wideband microwave tomography system with a novel frequency selection procedure," Apr. 2010, *IEEE Transactions on Biomedical Engineering*, 57(4):894-904.
Gilmore et al., "Corrections to the 'Enhancement of microwave tomography through the use of electrically conducting enclosures,'" Jan. 2010, *Inverse Problems*, 26(1):019801 (7 pgs.).
Gilmore et al., "Enhancement of microwave tomography through the use of electrically conducting enclosures," Apr. 8, 2008, *Inverse Problems*, 24(3): 035008 (21 pgs).
Gilmore et al., "Microwave Biomedical Data Inversion Using the Finite-Difference Contrast Source Inversion Method," May 2009, *IEEE Transactions on Antennas Propagation*, 57(5):1528-38.
Gilmore et al., "On super-resolution with an experimental microwave tomography system," 2010. *IEEE Antennas and Wireless Propagation Letters*, 9:393-96.
Gilmore et al., "The University of Manitoba Microwave Imaging Repository: A Two-Dimensional Microwave Scattering Database for Testing Inversion and Calibration Algorithms," Oct. 2011, *IEEE Antennas and Propagation Magazine*, 53(5):126-133.
Habashy et al., "A general framework for constraint minimization for the inversion of electromagnetic measurements," 2004, *Progress in Electromagnetics Research*, 46: 265-312.
Halter et al. "The correlation of in vivo and ex vivo tissue dielectric properties to validate electromagnetic breast imaging: initial clinical experience," 2009, *Physiological Measurement*, 30:S121-36.
Harrington. "Small resonant scatterers and their use for field measurements," 1962. *IRE Transactions on Microwave Theory and Techniques*, 10(3): 165-74.
Henriksson et al., "Quantitative microwave imaging for breast cancer detection using a planar 2.45 GHz system," Oct. 2010. *IEEE Transactions on Instrumentation and Measument*, 59(10):2691-99.
International Patent Application No. PCT/IB2014/067390, filed Dec. 29, 2014; International Search Report / Written Opinion dated May 5, 2015; 11 pages.
International Patent Application No. PCT/IB2014/067390, filed Dec. 29, 2014; International Preliminary Report on Patentability dated Jul. 14, 2016; 7 pages.
Joachimowicz et al., "Inverse Scattering: An Iterative Numerical Method for Electromagnetic Imaging," Dec. 1991, *IEEE Transactions on Antennas and Propagation*, 39(12):1742-53.
Kleinman et al., "A Modified gradient method for two-dimensional problems in tomography," 1992, *Journal of Computational and Applied Mathematics*, 42(1):17-35.
Klemm et al., "Radar-Based Breast Cancer Detection Using a Hemispherical Antenna Array—Experimental Results," Jun. 2009, *IEEE Transactions on Antennas and Propagation*, 57(6):1692-1704.
Lazebnik et al., "Highly Accurate Debye Models for Normal and Malignant Breast Tissue Dielectric Properties at Microwave Frequencies," Dec. 2007, *IEEE Microwave and Wireless Components Letters*, 17(12):822-24.
Lencrerot et al., "Imposing Zemike representation for imaging two-dimensional targets," Feb. 3, 2009, *Inverse Problems in Science and Engineering*, 25(3):035012 (21 pgs).
Lencrerot et al., "Measurement strategies for a confined microwave circular scanner," Sep. 2009, *Inverse Problems in Science and Engineering*, 17(6):787-802. [Available online Aug. 6, 2009].
LoVetri, Joe, "Computational electromagnetics and electromagnetic inverse imaging," Grant Abstract [online]. Natural Sciences and Engineering Research Council of Canada, project dates: fiscal year 2010-2011 [retrieved on Aug. 9, 2011]. Retrieved from the Internet: <:http://www.outil.ost.uqam.ca/CRSNG/Detail.aspx?Cle=451511 &Langue=2; 2 pgs.
Meaney et al., "A clinical prototype for active microwave imaging of the breast," Nov. 2000, *IEEE Transactions on Microwave Theory and Techniques*, 48(11):1841-53.
Meaney et al., "Initial clinical experience with microwave breast imaging in women with normal mammography," Feb. 2007, *Acad. Radial.*, 14(2): 207-18.
Meaney et al., "Microwave imaging for tissue assessment: initial evaluation in multitarget tissue-equivalent phantoms," Sep. 1996, *IEEE Transactions on Biomedical Engineering*, 43(9):878-90.
Meaney et al., "Nonactive antenna compensation for fixed-array microwave imaging: Part II—Imaging results," Jun. 1999, *IEEE Transactions on Medical Imaging*, 18(6):508-18.
Meaney et al., "Pre-scaled two-parameter Gauss-Newton image reconstruction to reduce property recovery imbalance," 2002, *Physics in Medicine and Biology*, 47(7):1101-19.
Memarzadeh-Tehran et al., "Optically modulated probe for precision near-field measurements," 2010. *IEEE Transactions on Instrumentation and Measurement*, 59(10):2755-62.
Mohassel, "Meander antennas". Ph.D. Dissertation. The University of Michigan. 1982.
Mojabi et al., "A Multiplicative Regularized Gauss-Newton Inversion for Shape and Location Reconstruction," Dec. 2011, *IEEE Transactions on Antennas and Propagation*, 59(12):4790-4802.
Mojabi et al., "A Novel Microwave Tomography System Using a Rotatable Conductive Enclosure," *IEEE Transactions on Antennas and Propagation*, May 2, 2011; 59(5): 1597-1605. Available online Mar. 7, 2011.
Mojabi et al., "Adapting the Normalized Cumulative Periodogram Parameter-Choice Method to the Tikhonov Regularization of 2-D/TM Electromagnetic Inverse Scattering Using Born Iterative Method," 2008, *Progress in Electromagnetics Research M*, 1:111-38.
Mojabi et al., "Biomedical microwave inversion in conducting cylinders of arbitrary shapes," *13th International Symposium on Antenna Technology and Applied Electromagnetics and the Canadian Radio Science Meeting (ANTEM/URSI)*, Toronto, Ontario, Feb. 15-18, 2009: 1-4.
Mojabi et al., "Comparison of TE and TM Inversions in the Framework of the Gauss—Newton Method," Apr. 2010, *IEEE Transactions on Antennas Propagation*, 58(4): 1336-48.
Mojabi et al., "Eigenfunction contrast source inversion for circular metallic enclosures," Feb. 2010, *Inverse Problems* 26(2):025010 (23 pgs.).
Mojabi et al., "Enhancement of the Krylov subspace regularization for microwave biomedical imaging," Dec. 2009, *IEEE Transactions on Medical Imaging*, 28(12): 2015-19. Available online Jul. 24, 2009.
Mojabi et al., "Microwave Biomedical Imaging Using the Multiplicative Regularized Gauss-Newton Inversion," 2009, *IEEE Antennas and Wireless Propagation Letters*, 8:645-48.
Mojabi et al. "Overview and classification of some regularization techniques for the Gauss-Newton inversion method applied to inverse scattering problems," Sep. 2009, *IEEE Transactions on Antennas and Propagation*, 57(9):2658-65.
Nikolova, "Microwave Imaging for Breast Cancer," Dec. 2011, *IEEE Microwave Magazine*, 12(7):78-94.
O'Halloran et al., "Rotating Antenna Microwave Imaging System for Breast Cancer Detection," 2010, *Progress in Electromagnetics Research*, 107:203-17.
Ostadrahimi et al., "A modified double layer tapered slot antenna with improved cross polarization" 2009. *13th International Symposium on Antenna Technology and Applied Electromagnetics and the Canadian Radio Sciences Meeting*. IEEE.
Ostadrahimi et al., "A Multiprobe-Per-Collector Modulated Scatterer Technique for Microwave Tomography," 2011, *IEEE Antennas and Wireless Propagation Letters*, 10:1445-48.
Ostadrahimi et al., "An MST-based microwave tomography system using homodyne receiver," 2013, *IEEE International Symposium on Antennas and Propagation and USNC/URSI National Radio Science Meeting*. IEEE. pp. 1-4.
Ostadrahimi et al., "A Near-Field Dual Polarized (TE-TM) Microwave Imaging System," Mar. 2013, *IEEE Transactions on Microwave Theory and Techniques*, (61)3:1376-84.
Ostadrahimi et al., "A Novel Microwave Tomography System Based on the Scattering Probe Technique," Feb. 2012, *IEEE Transactions on Instrumentation and Measurement*, 61(2):379-90.

(56) References Cited

OTHER PUBLICATIONS

Ostadrahimi et al., "Analysis of Incident Field Modeling and Incident/Ccattered Field Calibration Techniques in Microwave Tomography," 2011, *IEEE Antennas and Wireless Propagation Letters*, 10:900-03.

Ostadrahimi et al., "Enhancement of Gauss-Newton Inversion Method for Biological Tissue Imaging," Sep. 2013, *IEEE Transactions on Microwave Theory and Techniques*, 61(9):3424-34.

Ostadrahimi et al. "Investigating a double layer Vivaldi antenna design for fixed array field measurement". 2010. *Intl. Journal of Ultra Wideband Communications and Systems*. 1(4):282-290.

Ostadrahimi et al., "Slotted Waveguide Arrays for Collecting Near-Field Scattering Data" 2014, University of Manitoba—CancerCare Manitoba & Department of Physics and Astronomy, 1-2.

Pastorino, *Microwave Imaging*. John Wiley & Sons: Hoboken, New Jersey; 2010. Title Page, Copyright Page, Table of Contents, and Introduction, pp. 1-4.

Pastorino, "Stochastic Optimization Methods Applied to Microwave Imaging: A Review," Mar. 2007, *IEEE Transactions on Antennas and Propagation*, 55(3):538-48.

Paulsen et al., "Nonactive antenna compensation for fixed-array microwave imaging—Part I: Model development," Jun. 1999, *IEEE Transactions on Medical Imaging*, 18(6):496-507.

Rubæk et al., "Computational Validation of a 3-D Microwave Imaging System for Breast-Cancer Screening," Jul. 2009, *IEEE Transactions on Antennas and Propagation*, (57)7:2105-15.

Rubaek et al., "Nonlinear Microwave Imaging for Breast-Cancer Screening Using Gauss-Newton's Method and the CGLS Inversion Algorithm," Aug. 2007, *IEEE Transactions on Antennas and Propagation*, 55(8): 2320-31.

Semenov et al., "Microwave tomography: review of the progress towards clinical applications," 2009. *Philosophical Transactions of the Royal Society*, 367:3021-42.

Semenov et al., "Microwave tomography of extremities: 1. dedicated 2D system and physiological signatures," Apr. 7, 2011, *Physics in Medicine and Biology*, 56(7):2005-17.

Semenov et al. "Microwave-tomographic imaging of the high dielectric-contrast objects using different image-reconstruction approaches," Jul. 2005, *IEEE Transactions on Microwave Theory and Techniques*, 53(7):2284-94.

Semenov et al., "Spatial resolution of microwave tomography for detection of Myocardial Ischemia and infarction—experimental study on two-dimensional models," Apr. 2000. *IEEE Transactions on Microwave Theory and Techniques*, 48(4):538-44.

Stang et al., "A preclinical system prototype for focused microwave thermal therapy of the breast," Sep. 2012, *IEEE Transactions on Biomedical Engineering*, 59(9):2431-38.

Tijhuis et al., "Theoretical and Computational Aspects of 2-D Inverse Profiling," Jun. 2001, *IEEE Transactions on Geoscience and Remote Sensing*, 39(6):1316-30.

Van Den Berg et al., "A contrast source inversion method," 1997, *Inverse Problems*, 13(6):1607-20.

Vardalahos, "Investigation of Loaded Monopole Antenna," Ph.D. Dissertation. University of Leeds. 2000.

Wadbro et al., "Microwave Tomography Using Topology Optimization Techniques," Mar. 2008, *SIAM J Sci. Comput.*, 30(3):1613-33.

Wang et al., "An iterative solution of the two-dimensional electromagnetic inverse scattering problem," 1989, *Int. J. Imag. Syst. Technol.*, 1(1):100-08. Available online Oct. 20, 2005.

Yu et al., "Active Microwave Imaging II: 3-D System Prototype and Image Reconstruction From Experimental Data," Apr. 2008, *IEEE Transactions on Microwave Theory and Techniques*, 56(4):991-1000.

Zaeytijd et al., "Full-Wave Three-Dimensional Microwave Imaging With a Regularized Gauss-Newton Method—Theory and Experiment," Nov. 2007, *IEEE Transactions on Antennas and Propagation*, 55(11):3279-92.

Zakaria et al., "Application of multiplicative regularization to the finite-element contrast source inversion method," Sep. 2011, *IEEE Transactions on Antennas and Propagation*, 59(9):3495-98.

Zakaria et al., "Finite-element contrast source inversion method for microwave imaging," 2010, *Inverse Problems*, 26:115010.

Zakaria et al., "The Finite-Element Method Contrast Source Inversion Algorithm for 2D Transverse Electric Vectorial Problems," Oct. 2012, *IEEE Transactions on Antennas and Propagation*, 60(10):4757-65.

Zakaria et al., "Full-vectorial parallel finite-element contrast source inversion method," 2013, *Progress in Electromagnetics Research*, 142:463-83.

Harrington. *Time Harmonic Electromagnetic Fields*, 2001. Dudley (Ed.) John Wiley & Sons, Inc.: New York. Cover Page, Copyright Page, Table of Contents, Preface.

Semenov et al., "Three-dimensional microwave tomography: initial experimental imaging of animals," Jan. 2002, *IEEE Transactions on Biomedical Engineering*, 49(1):55-63.

\* cited by examiner

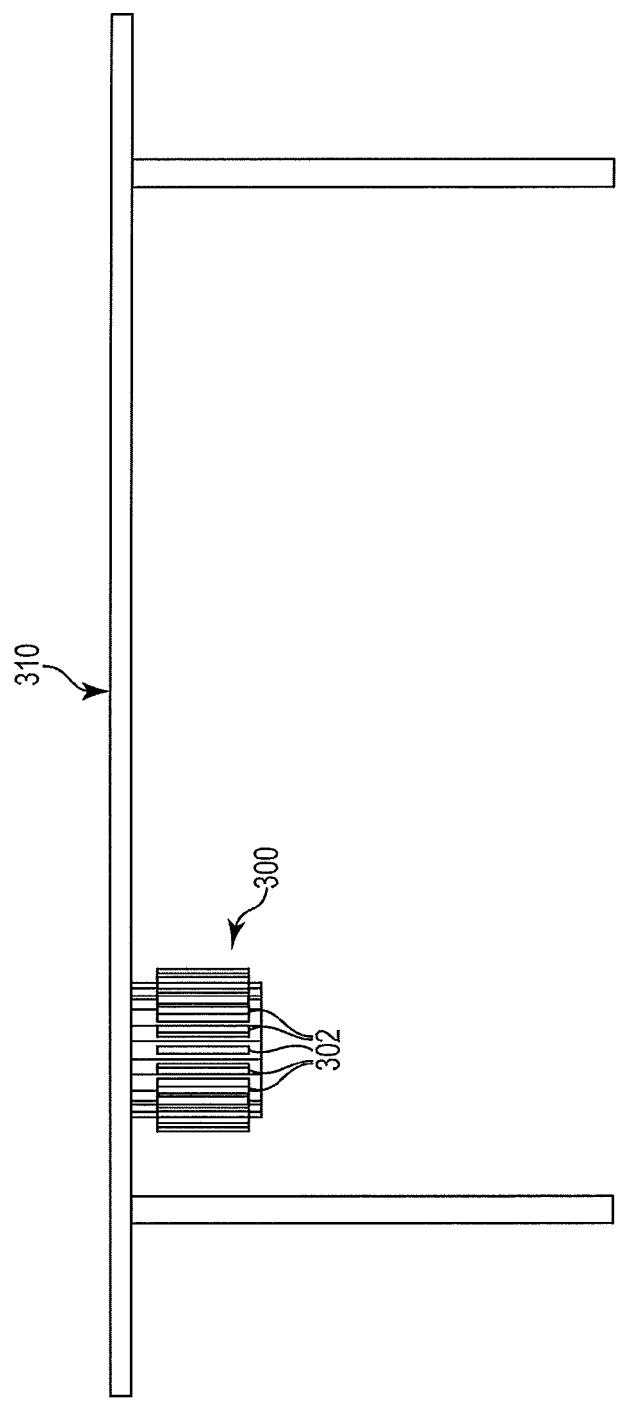

IMAGING USING GATED ELEMENTS

CROSS-REFERENCE TO RELATED APPLICATION

This application is the § 371 U.S. National Stage of International Application No. PCT/IB2014/067390, filed 29 Dec. 2014, which claims the benefit of U.S. Provisional Application Ser. No. 61/921,808 filed on 2013 Dec. 30 entitled "IMAGING USING GATED ELEMENTS," each of which is incorporated herein by reference in their entireties.

BACKGROUND

The present disclosure pertains to imaging systems and imaging methods, e.g., microwave and millimeter wave energy based imaging, using waveguide assemblies including one or more gated elements.

In the art of microwave imaging (MWI), an object of interest (OI) is illuminated by microwave energy and the scattered fields are collected outside the OI. The collected scattered fields may then be used to reconstruct qualitative, and possibly quantitative images, or interior maps, of the OI that include its location, geometry, shape, magnetic properties, and dielectric properties. The ability to provide quantitative imaging and to utilize non-ionizing radiations associated with MWI make MWI a good candidate for use in many novel applications such as non-destructive testing in industrial applications, non-invasive imaging of biological tissues, remote sensing, geophysical survey of underground objects, and other security and military applications.

Due to the inherent non-linear and ill-posed behavior of the inverse scattering problem used in MWI, a substantial amount of electromagnetic scattering data may need to be collected in order to ensure a robust inversion and quantitatively-accurate image. The need for more data can be satisfied by several approaches such as, e.g., increasing the number of data acquisition points, using different frequencies, collecting multiple field polarizations, etc.

Microwave imaging has been deployed in many biomedical, security, and industrial applications such as breast cancer diagnostics (see, e.g., N. Nikolova, "Microwave imaging for breast cancer," Microwave Magazine, IEEE, vol. 12, no. 7, pp. 78-94, December 2011), biological tissue imaging (see, e.g., M. Ostadrahimi, P. Mojabi, A. Zakaria, J. LoVetri, and L. Shafai, "Enhancement of Gauss-Newton inversion method for biological tissue imaging," Microwave Theory and Techniques, IEEE Transactions on, vol. 61, no. 9, pp. 3424-3434, 2013), non-destructive testing and evaluation (see, e.g., R. Zoughi, M. A. AbouKhousa, M. T. A. Ghasr, S. Kharkivskiy, and D. Pommerenke, "Microwave and millimeter wave imaging system,", U.S. Pat. No. 7,746,266; and M. Ghasr, M. Abou-Khousa, S. Kharkovsky, R. Zoughi, and D. Pommerenke, "Portable real-time microwave camera at 24 GHz," Antennas and Propagation, IEEE Transactions on, vol. 60, no. 2, pp. 1114-1125, February 2012), and geophysical surveying (see, e.g., A. Abubakar and P. Van Den Berg, "Non-linear three-dimensional inversion of cross-well electrical measurements," Geophysical prospecting, vol. 48, no. 1, pp. 109-134, 2000).

The basic operation of a MWI system is based on illuminating an object-of-interest (OI) by a transmitting antenna and collecting the scattered fields at various receiving locations. The collected field data may be calibrated and then processed using non-linear inverse scattering algorithms (see, e.g., Q. Fang, P. Meaney, and K. Paulsen, "Viable three-dimensional medical microwave tomography: theory and numerical experiments," Antennas and Propagation, IEEE Transactions on, vol. 58, no. 2, pp. 449-458, 2010; J. De Zaeytijd, A. Franchois, C. Eyraud, and J. Geffrin, "Full-wave three-dimensional microwave imaging with a regularized Gauss-Newton method theory and experiment," Antennas and Propagation, IEEE Transactions on, vol. 55, no. 11, pp. 3279-3292, 2007; A. Zakaria, C. Gilmore, and J. LoVetri, "Finite-element contrast source inversion method for microwave imaging," Inverse Problems, vol. 26, p. 115010, 2010; and P. Mojabi and J. LoVetri, "Microwave biomedical imaging using the multiplicative regularized Gauss-Newton inversion," Antennas and Wireless Propagation Letters, IEEE, vol. 8, pp. 645-648, 2009) or radar techniques (see, e.g., M. Klemm, I. Craddock, J. Leendertz, A. Preece, and R. Benjamin, "Radar-based breast cancer detection using a hemispherical antenna array experimental results," Antennas and Propagation, IEEE Transactions on, vol. 57, no. 6, pp. 1692-1704, 2009).

Depending on the application, the imaging results, or outcome, may be either a quantitative reconstruction of the complex dielectric and magnetic profile of the OI that provides information on its shape and location and/or a qualitative image that produces the shadow of the OI. The microwave imaging providing qualitative imaging method may not incur a heavy computational burden (e.g., such as quantitative MWI) and may be accomplished in real-time. Although qualitative imaging may provide some information about the internal structure and composition of an OI, qualitative imagine may not provide the ability to identify materials, such as, e.g., tissues, etc., in a reconstructed image as well as quantitative MWI may be able to provide (e.g. which may be helpful in biomedical and geo-surveying applications). Further, quantitative images can be processed and interpreted by intelligent computer algorithms due to the known values of the dielectric properties of materials and biological tissues, which may accelerate image interpretation by skilled technicians, radiologists, and trained human resources.

In order to obtain a quantitative interior image of an OI, microwave energy should penetrate sufficiently into the object. To reduce reflections from the boundary of the OI, and thus maximize field penetration, the OI may be immersed into a matching fluid (see, e.g., C. Gilmore, A. Zakaria, J. LoVetri, and S. Pistorius, "A study of matching fluid loss in a biomedical microwave tomography system," Medical physics, vol. 40, p. 023101, 2013). Furthermore, because wave penetration depth is inversely proportional to the frequency of operation, upper limits on the frequency that can be used may exist, especially when imaging biological targets. Further, microwave imaging systems used for biomedical applications may operate up to X-band such as, e.g., 915 MHz (see, e.g., J. Stang, M. Haynes, P. Carson, and M. Moghaddam, "A preclinical system prototype for focused microwave thermal therapy of the breast," Biomedical Engineering, IEEE Transactions on, 2012, early access), 1.0-2.3 GHz (see, e.g., S. Semenov, J. Kellam, Y. Sizov, A. Nazarov, T. Williams, B. Nair, A. Pavlovsky, V. Posukh, and M. Quinn, "Microwave tomography of extremities: 1. dedicated 2D system and physiological signatures," Physics in Medicine and Biology, vol. 56, p. 2005, 2011), 2.45 GHz (see, e.g., A. Franchois, A. Joisel, C. Pichot, and J. Bolomey, "Quantitative microwave imaging with a 2.45-GHz planar microwave camera," Medical Imaging, IEEE Transactions on, vol. 17, no. 4, pp. 550-561, 1998), 0.9-1.5 GHz (see, e.g., P. Meaney, M. Fanning, T. Raynolds, C. Fox, Q. Fang, C. Kogel, S. Poplack, and K. Paulsen, "Initial clinical experience with microwave breast imaging in women with normal mammography," Academic Radiology, vol. 14, no. 2, pp. 207-218, 2007), 2-8 GHz (see, e.g., E. C. Fear, M. A. Stuchly, "Microwave Detection of Breast Cancer," Microwave Theory and Techniques, IEEE Transactions on, vol. 48, pp. 1854-1863, November 2000), and/or 4-9 GHz (see, e.g., M. Klemm, I. J. Craddock, J. A. Leendertz, A. Preece, R. Benjamin, "Radar-Based Breast Cancer Detection Using a Hemispherical Antenna Array—Experimental Results," Antennas and Propagation, IEEE Transactions on, vol. 57, no. 6, pp. 1692-1704, June 2009).

Due to the low operational frequency and the compact size of MWI systems, a target may be located in the near-field region of the antennas. In this region, complicated field distributions may exist due to the presence of some or all polarizations, arbitrary wave impedances, and both propagating as well as evanescent modes. Further, polarization may be utilized in microwave imaging and may not be generally available in other imaging modalities. The use of different polarizations in MWI may require the use of inversion algorithms capable of inverting vector field problems; specialized measurement techniques sensitive to individual polarizations; and proper calibration techniques. The ability to use arbitrary polarizations of electromagnetic energy may further require full-wave computational models of the imaging chamber (see, e.g., M. Ostadrahimi, P. Mojabi, C. Gilmore, A. Zakaria, S. Noghanian, S. Pistorius, and J. LoVetri, "Analysis of incident field modeling and incident/scattered field calibration techniques in microwave tomography," Antennas and Wireless Propagation Letters, IEEE, vol. 10, pp. 900-903, 2011). Such full-wave modeling of the imaging system may be computationally expensive. Further, the measurement of different polarizations may require sophisticated experimental systems that can differentiate between measured signal polarizations. Still further, associated calibration techniques for full-wave modeling may need to be tailored for each polarization and for the specific measurement system being used.

Due to these challenges, existing imaging systems may collect data only in a two-dimensional (2-D) plane, while measuring only a single field polarization in the near-field region (see, e.g., Q. Fang, P. Meaney, and K. Paulsen, "Viable three-dimensional medical microwave tomography: theory and numerical experiments," Antennas and Propagation, IEEE Transactions on, vol. 58, no. 2, pp. 449-458, 2010; S. Semenov, J. Kellam, Y. Sizov, A. Nazarov, T. Williams, B. Nair, A. Pavlovsky, V. Posukh, and M. Quinn, "Microwave tomography of extremities: 1. dedicated 2D system and physiological signatures," Physics in Medicine and Biology, vol. 56, p. 2005, 2011; and T. Henriksson, N. Joachimowicz, C. Conessa, and J. Bolomey, "Quantitative microwave imaging for breast cancer detection using a planar 2.45 GHz system," Instrumentation and Measurement, IEEE Transactions on, vol. 59, no. 10, pp. 2691-2699, 2010). A few 3-D MWI systems exists that only collect a single field polarization (see, e.g., T. Rubæk, O. Kim, and P. Meincke, "Computational validation of a 3-D microwave imaging system for breast-cancer screening," Antennas and Propagation, IEEE Transactions on, vol. 57, no. 7, pp. 2105-2115, 2009) or place the antennas in the far-field region and rotate the antennas to collect two field polarizations (see, e.g., J. Geffrin and P. Sabouroux, "Continuing with the Fresnel database: experimental setup and improvements in 3D scattering measurements," Inverse Problems, vol. 25, p. 024001, 2009). Further, 2-D MWI systems using antennas to directly measure fields have been designed and implemented (see, e.g., C. Gilmore, A. Zakaria, P. Mojabi, M. Ostadrahimi, S. Pistorius, and J. LoVetri, "The University of Manitoba microwave imaging repository: a two-dimensional microwave scattering database for testing inversion and calibration algorithms," Antennas and Propagation Magazine, IEEE, vol. 53, no. 5, pp. 126-133, October 2011), as well as other systems using remote probes based on the Modulated Scattering Technique (MST) (see, e.g., M. Ostadrahimi, P. Mojabi, S. Noghanian, L. Shafai, S. Pistorius, and J. LoVetri, "A novel microwave tomography system based on the scattering probe technique," Instrumentation and Measurement, IEEE Transactions on, vol. 61, no. 2, pp. 379-390, February 2012).

In at least one MWI approach, some field measurement probes distributed at various locations have been used to infer the electromagnetic field impinging on their location. By changing/modulating the impedance of each probe, its interaction with the electromagnetic field is changed/modulated. The change/modulation of the interaction may then be detected by an antenna, referred to as the collector antenna, at some distances from the probe. The detected modulated signal at the collector antenna was shown to be proportional to the field at the probe's location, which may be referred to as the Modulated Scattering Technique (MST).

MST-based MWI systems may provide several advantages such as, e.g., accurate near-field measurement, robust calibration, inexpensive experimental implementation, collecting various field polarizations (see, e.g., M. Ostadrahimi, A. Zakaria, J. LoVetri, and L. Shafai, "A near-field dual polarized TE-TM microwave imaging system," Microwave Theory and Techniques, IEEE Transactions on, vol. 61, no. 3, pp. 1376-1384, 2013), and an increased amount of nonredundant data (see, e.g., M. Ostadrahimi, P Mojabi, S. Noghanian, J. LoVetri, and L. Shafai, "A multiprobe-percollector modulated scatterer technique for microwave tomography," Antennas and Wireless Propagation Letters, IEEE, vol. 10, pp. 1445-1448, 2011). One MST-based system may utilize probes that are printed dipoles and consist of 5 p-i-n diodes in series. The impedance of the probes may have two cases: the diodes may be forward biased; and the diodes may be reversed biased. In each case, the probe's perturbation of the electromagnetic field is detected by a collector antenna using a Vector Network Analyzer (VNA) (see, e.g., M. Ostadrahimi, P. Mojabi, S. Noghanian, L. Shafai, S. Pistorius, and J. LoVetri, "A novel microwave tomography system based on the scattering probe technique," Instrumentation and Measurement, IEEE Transactions on, vol. 61, no. 2, pp. 379-390, February 2012; and M. Ostadrahimi, A. Zakaria, J. LoVetri, and L. Shafai, "A near-field dual polarized TE-TM microwave imaging system," Microwave Theory and Techniques, IEEE Transactions on, vol. 61, no. 3, pp. 1376-1384, 2013) or a custom-designed coherent receiver (see, e.g., M. Ostadrahimi, M. Asefi, J. LoVetri, G. Bridges, and L. Shafai, "An mst-based microwave tomography system using homodyne receiver," in IEEE International Symposium on Antennas and Propagation and USNC/URSI National Radio Science Meeting. IEEE, 2013, pp. 1-4).

SUMMARY

One exemplary method of imaging an object using microwave imaging may include providing a plurality of waveguide assemblies positioned about an object. Each waveguide assembly of the plurality of waveguide assemblies may include a waveguide structure configured to deliver and sample electromagnetic energy (e.g., guide or direct electromagnetic energy to be delivered and/or sampled) and one or more gated elements (e.g., two or more gated elements).

In at least one embodiment, the waveguide structure may define an enclosed volume for confining electromagnetic energy therein. Further, each gated element of the one or more gated elements may define an aperture extending into the waveguide structure (e.g., the enclosed volume defined by the waveguide structure), and each gated element of the one or more gated elements may be configurable in at least a transmission state, a reception state, and a passive state. Each gated element of the one or more gated elements may be configured to radiate electromagnetic energy when in the transmission state, to collect electromagnetic energy when in the reception state, and to neither radiate nor collect electromagnetic energy when in the passive state. The exemplary method may further include delivering electromagnetic energy using at least one waveguide assembly of the plurality of waveguide assemblies (e.g., using at least one gated element of the at least one waveguide assembly) to irradiate the object resulting in scattered electromagnetic energy, sampling the scattered electromagnetic energy using at least one waveguide assembly of the plurality of waveguide assemblies (e.g., using at least one gated element of the at least one waveguide assembly), and reconstructing an image of the object (e.g., quantitative image) based on the sampled scattered electromagnetic energy.

One exemplary system for use in imaging an object using microwave imaging may include a plurality of waveguide assemblies positioned about an object. Each waveguide assembly of the plurality of waveguide assemblies may include a waveguide structure configured to deliver and sample electromagnetic energy (e.g., guide or direct electromagnetic energy to be delivered and/or sampled) and one or more gated elements (e.g., two or more gated elements). In at least one embodiment, the waveguide structure may define an enclosed volume for confining electromagnetic energy therein. Further, each gated element of the one or more gated elements may define an aperture extending into the waveguide structure (e.g., an enclosed volume defined by the waveguide structure) and each gated element of the one or more gated elements may be configurable in at least a transmission state, a reception state, and a passive state. Each gated element of the one or more gated elements may be configured to radiate electromagnetic energy when in the transmission state, to collect electromagnetic energy when in the reception state, and to neither radiate nor collect electromagnetic energy when in the passive state. The exemplary system may include processing apparatus coupled to the plurality of waveguide assemblies and the processing apparatus may be configured to deliver electromagnetic energy using at least one waveguide assembly of the plurality of waveguide assemblies to irradiate the object resulting in scattered electromagnetic energy, sample the scattered electromagnetic energy using at least one waveguide assembly of the plurality of waveguide assemblies, and reconstruct an image of the object (e.g., quantitative image) based on the sampled scattered electromagnetic energy.

In one or more embodiments, to sample the scattered electromagnetic energy using at least one waveguide assembly of the plurality of waveguide assemblies, a modulation signal may be applied to an individual gated element to configure the individual gated element into the reception state. Further, the modulation signal may have a lower frequency than the electromagnetic energy delivered using at least one waveguide assembly of the plurality of waveguide assemblies.

In one or more embodiments, sampling the scattered electromagnetic energy using at least one waveguide assembly of the plurality of waveguide assemblies may include sampling the scattered electromagnetic energy using each gated element individually of the one or more gated elements of each waveguide assembly of the plurality of waveguide assemblies until each gated element of the one or more gated elements of the plurality of waveguide assemblies has been individually used to sample the scattered electromagnetic energy. Further, to sample the scattered electromagnetic energy using each gated element individually, a selected gated element may be configured in the reception state, the remaining gated elements of the one or more gated elements of the plurality of waveguide assemblies may be configured in the passive state except for the one more gated elements configured in the transmission state to deliver the electromagnetic energy, and the waveguide assembly including the selected gated element may sample the scattered electromagnetic energy.

In one or more embodiments, delivering electromagnetic energy using at least one waveguide assembly of the plurality of waveguide assemblies may include delivering the electromagnetic energy using each gated element individually of the one or more gated elements of each waveguide assembly of the plurality of waveguide assemblies until each gated element of the one or more gated elements of the plurality of waveguide assemblies has been individually used to deliver the electromagnetic energy. Further, to deliver the electromagnetic energy using each gated element individually, a selected gated element may be configured in the transmission state, the remaining gated elements of the one or more gated elements of the plurality of waveguide assemblies may be configured in the passive state except for the one or more gated elements configured in the reception state for sampling the scattered electromagnetic energy, and the waveguide assembly including the selected gated element may deliver the electromagnetic energy to radiate from the selected gated element.

In one or more embodiments, each waveguide assembly of the plurality of waveguide assemblies may be configured to provide a standing wave within the waveguide structure (e.g., the enclosed volume defined by the waveguide structure) when electromagnetic energy is being delivered therefrom. Further, each waveguide assembly of the plurality of waveguide assemblies may extend from a first end portion to a second end portion, and each of the first and the second end portion may be configured for a shorting boundary condition to provide the standing wave. Further, the waveguide structure of each waveguide assembly of the plurality of waveguide assemblies may include a conductive wall portion (e.g., extending around an enclosed volume) and defining an opening and a gated element portion positioned over the opening. Further, the gated element portion may include a printed circuit board. Still further, the gated element portion may include a conductive layer conductively coupled to the at least one conductive wall portion. Yet further, the gated element portion may include a pair of electrical traces for each of the one or more gated elements, and the electrical traces may be electrically shielded from electromagnetic energy directed, or guided, by the waveguide structure (e.g., electromagnetic energy within the enclosed volume of the waveguide structure).

In one or more embodiments, each gated element of the one or more gated elements may include one or more switchable segments configurable between a conducting configuration (e.g., low impedance configuration) and a non-conducting configuration (e.g., high impedance configuration). The switchable segment may be configured in the conducting configuration when the gated element is in the passive state and the switchable segment may be configured in the non-conducting configuration when the gated element is the transmission state.

In one or more embodiments, the aperture of each gated element may define a length that is half the wavelength of the electromagnetic energy delivered by the plurality of waveguide assemblies. Further, the aperture of each gated element may define a slot. The slot may define a width and a length perpendicular to width, and the length may be greater than the width.

In one or more embodiments, the one or more gated elements may include at least one gated element to collect electromagnetic energy of a first selected polarization when in the reception state and at least one gated element to collect electromagnetic energy of a second selected polarization different that the first selected polarization when in the reception state. Further, the first selected polarization may be perpendicular to the second selected polarization.

In one or more embodiments, each waveguide assembly of the plurality of waveguide assemblies may define a fluid gate configured to allow matching fluid to flow into and out of the waveguide structure (e.g., an enclosed volume of the waveguide structure).

In one or more embodiments, the plurality of waveguide assemblies may be in a fixed position relative to the object, configured to be attached to the object, and/or positioned around a perimeter of the object to form at least a portion of an imaging chamber.

Exemplary three-dimensional multi-polarized microwave imaging systems described herein may be robust, inexpensive, and manufacturable with a high degree of consistency and accuracy. The exemplary systems may be adapted to various biomedical, clinical, and industrial imaging applications. Further, the exemplary systems may include an array of multiplexed transmitting/collecting waveguides each of which are equipped with a plurality of gated elements (e.g., printed precisely on a printed-circuit-board). The waveguide-gated element pairs may then be positioned next to each other as a closed-chain around an object of interest. Each gated element may define a slot on the circuit board and be equipped with at least one p-i-n diode (e.g., one, five, a plurality, etc.) that is located in the center of the slot. The diode may be biased in three different states (open/non-conducting, short/conducting, or modulated/both non-conducting and conducting). The diode, when open, may enable the gated element to illuminate an object of interest by microwave energy, the diode, when modulated, may be configured to measure an electromagnetic field scattered by the object of interest based on a modulated scattering technique (MST).

The gated elements may be oriented vertically, horizontally, slanted, or perpendicular to the measurement chamber. Different orientations can collect various field polarizations such as, e.g., transverse electric (TE), transverse magnetic (TM), normal field, a combination of different polarizations, etc. without the need for mechanical movement. In one or more embodiments, to illuminate the object with all possible polarizations of an electromagnetic field, the gated elements can be configured in arbitrary orientations. The data collected using the gated elements and waveguides may be calibrated based on the orientation/polarization of the gated elements. The calibrated data can then be used to reconstruct the dielectric and/or magnetic profiles of various objects using either two-dimensional or three-dimensional inversion algorithms. Further, in one or more embodiments, a highly-sensitive coherent receiver may improve the sensitivity of the system, which may allow one to decrease the illuminated power to the object (e.g., low power illumination may be useful for biomedical applications, which may be limited on the amount of the exposed power).

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 18A is a side elevation view of an exemplary system using the exemplary imaging system of FIG. 9 for use in, e.g., imaging a female breast.

DETAILED DESCRIPTION OF EXEMPLARY EMBODIMENTS

Figure 1:
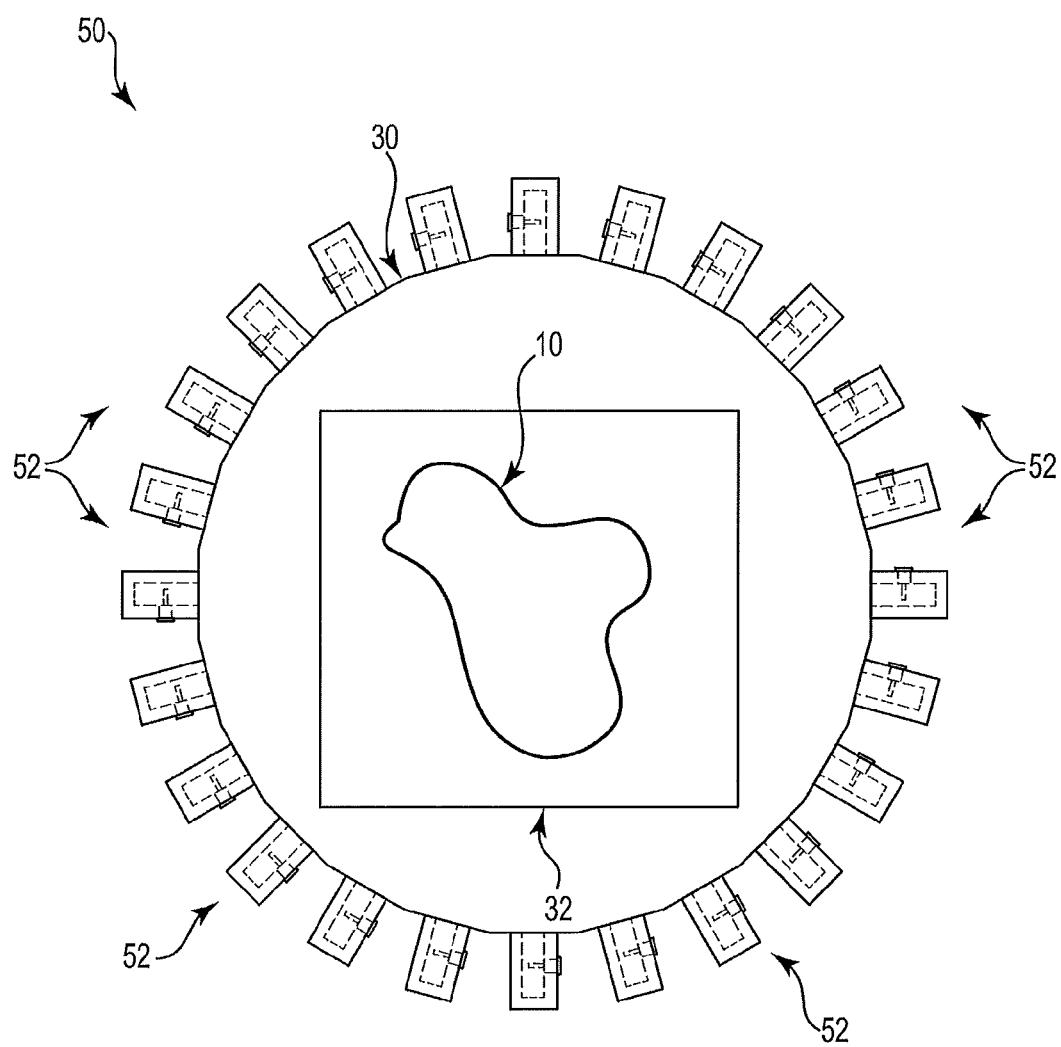
FIG. 1 is a plan view of an exemplary imaging setup.

Exemplary systems and methods described herein may be configured to implement a 2-D and/or 3-D vectorial MWI system with a high degree of accuracy and consistency. Further, the exemplary systems and methods may be inexpensive, based on a microwave scattering technique, and may use printed-circuit-board (PCB) technology. The exemplary systems and methods may use gated elements (e.g., defining slots) that not only collect the field but also illuminate an object of interest (OI) with different polarizations. In order to deliver/collect radiofrequency (RF) signals to/from each gated element, one or more waveguides may be used. The waveguides may be integrated with the gated elements to provide waveguide assemblies. Each waveguide assembly may include any number of gated elements and the gated elements may have one or more different orientations (e.g., configured for different polarizations). Further, the gated elements may be electronically controlled to operate either as a transmitter, a receiver, or neither. In one or more embodiments, the gated elements may be manufactured on printed circuit boards, and thus, may be manufactured consistently and accurately. Furthermore, biasing wires or traces used to bias the gated elements may be configured (e.g., specifically routed, shielded from the waveguides, shield from the measurement domain, shielded from the imaging domain etc.) so as to not interfere with the microwave imaging operation and processes.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, apparatus, and systems shall be described with reference to FIGS. 1-18. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

An exemplary imaging setup 50, or configuration, is depicted in FIG. 1. The imaging setup 50 includes a plurality of waveguide assemblies 52 configured to deliver and sample electromagnetic energy. More specifically, the waveguide assemblies 52 may be described as being able to direct, or guide, electromagnetic energy for delivery to the object of interest 10 and sample electromagnetic energy (e.g., electromagnetic energy scattered after being delivered to the object of interest 10).

The plurality of waveguide assemblies 52 may be positioned about an object of interest 10. For example, the plurality of waveguide assemblies 52 may be positioned completely around the object of interest (OI) 10. Further, although not shown, the plurality of waveguide assemblies 52 may be positioned partially around the object of interest 10 such as one quarter around the OI 10, halfway around the OI 10, three quarters around the OI 10, etc. The exemplary imaging setups 50 described herein may include any number of waveguide assemblies. For example, the exemplary imaging setups 50 may include 2 or more waveguide assemblies, 3 or more waveguide assemblies, 5 or more waveguide assemblies, 6 or more waveguide assemblies, 7 or more waveguide assemblies, 10 or more waveguide assemblies, 12 or more waveguide assemblies, 16 or more waveguide assemblies, 24 or more waveguide assemblies, etc. Further, the exemplary imaging setups 50 may include 50 or less waveguide assemblies, 40 or less waveguide assemblies, 36 or less waveguide assemblies, 30 or less waveguide assemblies, 24 or less waveguide assemblies, 18 or less waveguide assemblies, 16 or less waveguide assemblies, 8 or less waveguide assemblies, etc.

As shown in FIG. 1, the exemplary imaging setup 50 includes 24 waveguide assemblies 52 spaced about the object of interest 10 defining a measurement domain 30. The measurement domain 30 may be defined as the area within an electromagnetic scattered field created by the imaging setup 50 within which data may be gathered using the imaging setup 50. Further, the imaging setup 50 may be configured to image an imaging domain 32 containing the object 10 located within the measurement domain 30. The imaging domain 32 may be a subset, or portion, of the measurement domain 30.

The waveguide assemblies 52 of the imaging setup 50 may be located about the object 10 in any spacing and/or distance from the object 10 so as to be able to provide scattering data (e.g., measurements with respect to a scattered electromagnetic field resulting from delivering electromagnetic energy to the object of interest) useful for the reconstruction of an image of the object 10. The waveguide assemblies 52 may be in a fixed position relative to each other and/or to the object 10 during imaging such that the position of the waveguide assemblies does not change during imaging. For example, the waveguide assemblies 52 may be attached to a structure such as a measurement chamber within which the object 10 may be located. In at least one embodiment, the waveguide assemblies 52 may be positioned around a perimeter of the object. The waveguide assemblies 52 may form part of or the entire measurement chamber. For example, the measurement chamber may be a chamber of any shape defining the measurement domain 30.

Further, for example, the waveguide assemblies 52 may be attached to the object 10 itself. In at least one embodiment, the waveguide assemblies 52 may be attached to a belt-like apparatus that may be wrapped around the object 10.

To provide useful scattering data for reconstruction of an image of the object 10, the positions, or locations, of the waveguide assemblies 52 with respect to each other must be known or determined. When the waveguide assemblies 52 are attached to a structure, the positions of the waveguide assemblies 52 are already known (e.g., due to being fixed to the structure). When the waveguide assemblies 52 are not attached to a structure, and instead attached to the object 10 itself or not-fixedly arranged prior to imaging, a calibration procedure may be executed to determine the positions/locations of the waveguide assemblies prior to imaging as described further herein.

As shown in FIG. 1, the waveguide assemblies 52 are located equidistantly from the center of the imaging domain 32 and spaced equidistantly from each other. In other embodiments, the waveguide assemblies 52 may not be equidistantly from the center of the imaging domain 32 and/or spaced equidistantly from each other.

Figure 2:
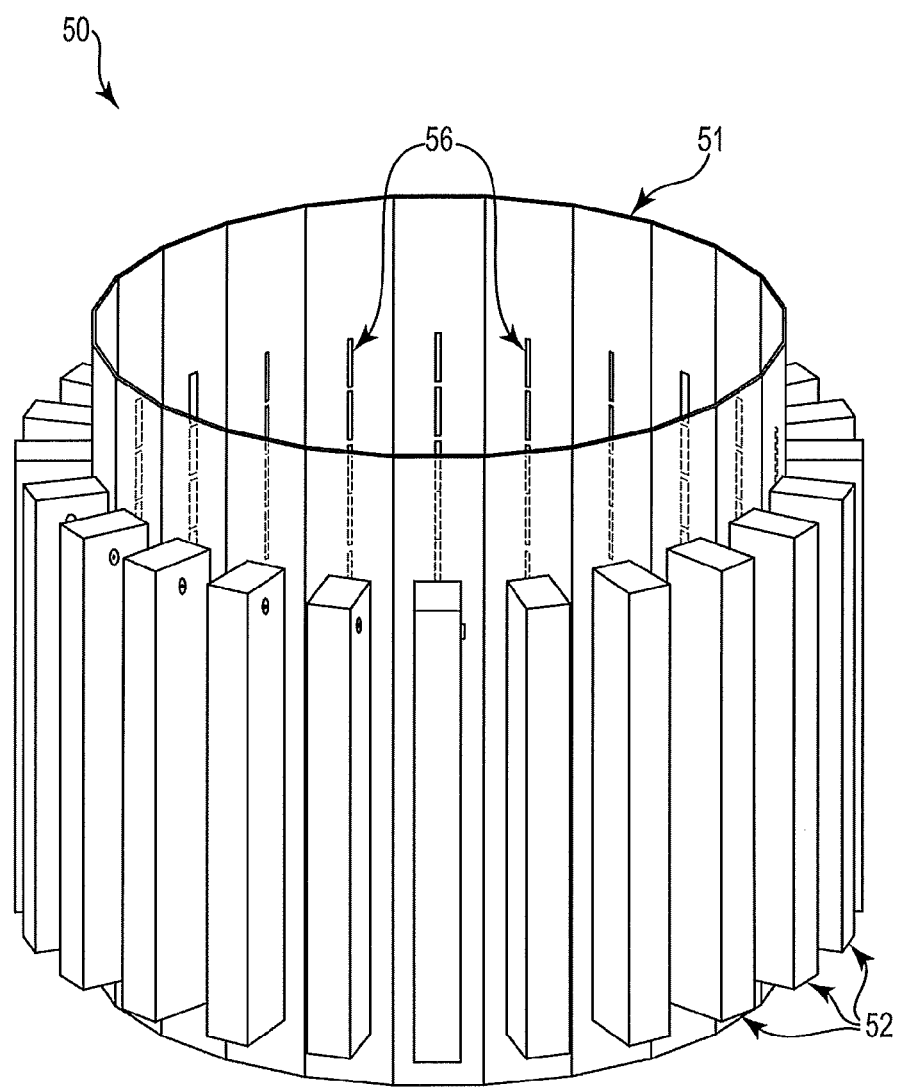
FIG. 2 is a perspective view of an exemplary imaging setup.

A perspective view of the exemplary imaging setup 50 of FIG. 1 is depicted in FIG. 2. As shown, the plurality of waveguide assemblies 52 may be attached, or coupled, to a measurement chamber 51 and positioned thereabout. The object of interest may be located in the measurement chamber 51 and the measurement chamber may define the measurement domain 30. As described herein, the waveguide assemblies 52 may be described as forming part or the entire of the measurement chamber 51. For example, the measurement chamber 51 may include a plurality of waveguide assemblies 52 positioned adjacent each other to form a cylindrical measurement domain. Further, for example, the measurement chamber 51 may include a plurality of waveguide assemblies 52 positioned around the cylindrical measurement domain with spacer material or portions positioned between each waveguide assembly 52 (e.g., the waveguide assemblies 52 may be not be positioned adjacent).

Figure 3A:
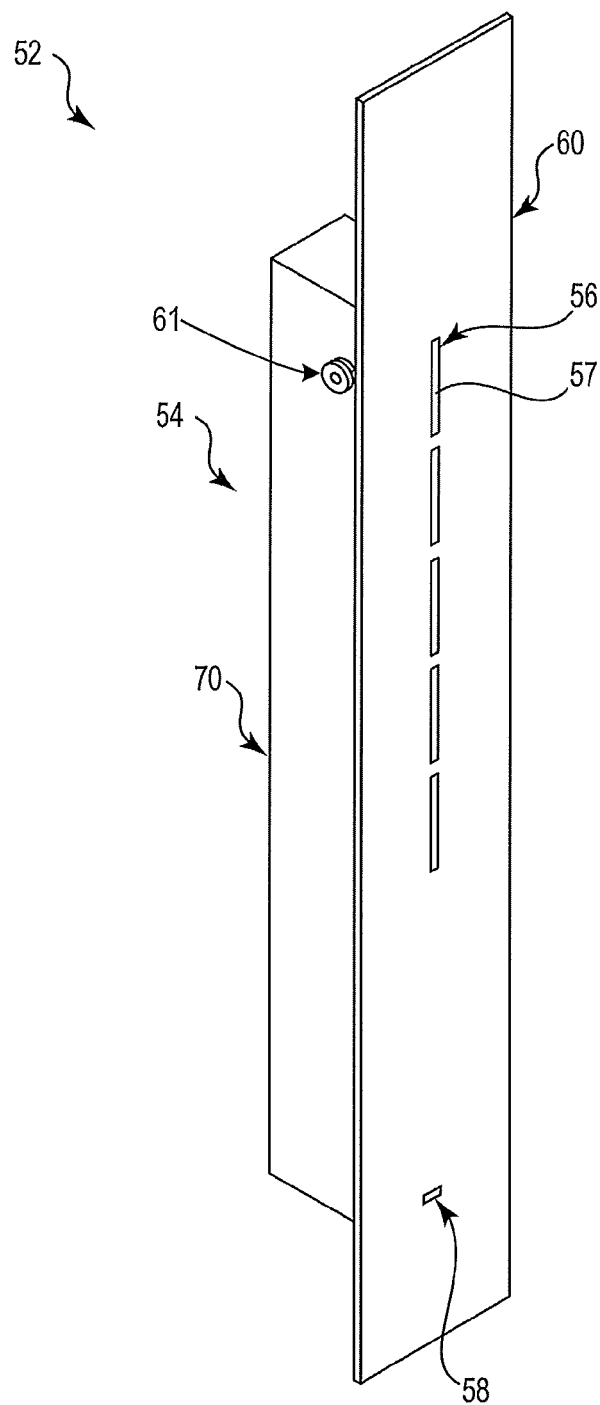
FIG. 3A is perspective view of an exemplary waveguide assembly of the imaging setup of FIGS. 1-2.
Figure 3B:
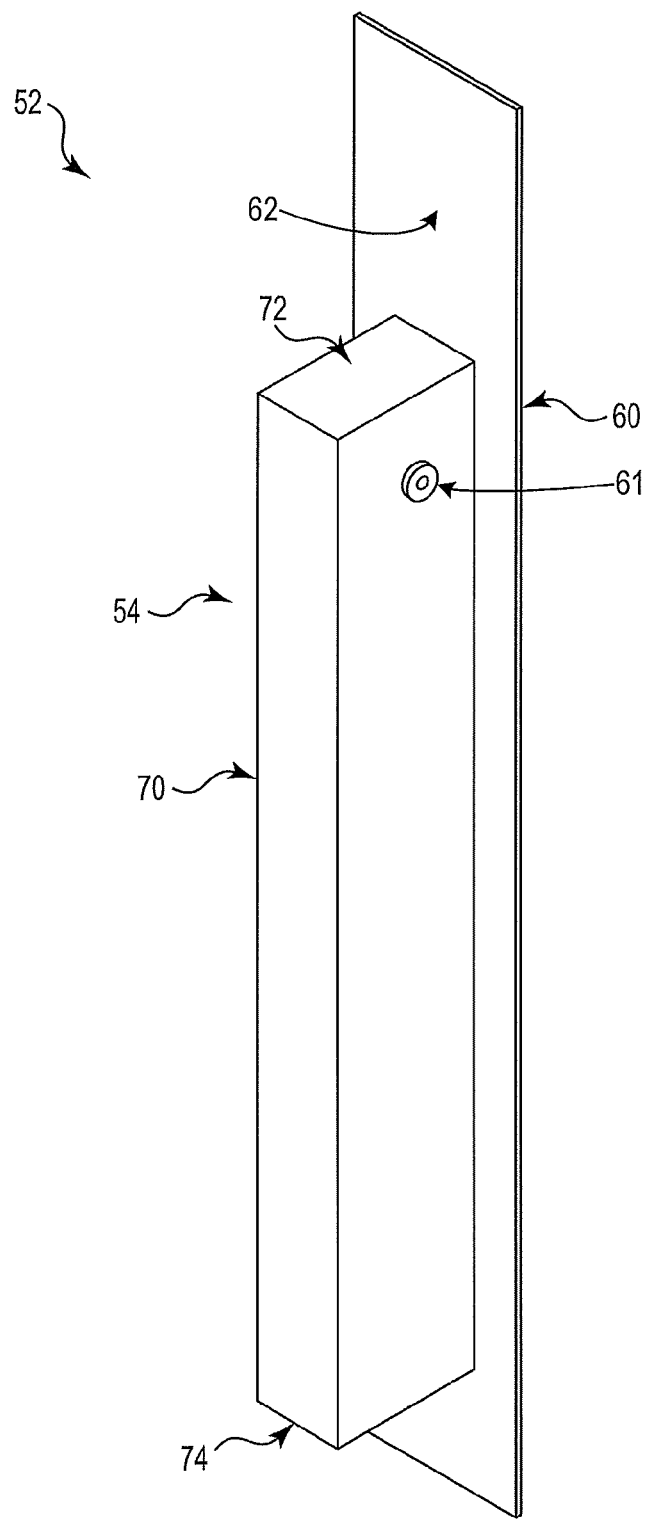
FIG. 3B is rear perspective view of the exemplary waveguide assembly of FIG. 3A.

Each of the waveguide assemblies 52, which are shown in more detail in FIGS. 3A-3B, may include a waveguide structure 54 defining an enclosed volume for confining electromagnetic energy therein. In other embodiments, exemplary waveguide structures may not enclosed a volume or define an enclosed volume for confining electromagnetic energy therein. For example, exemplary waveguide structures may define a structure, or structures, configured to direct electromagnetic energy to a location to be collected, or sampling, for using in imaging as described further herein. In at least one embodiment, the exemplary waveguide structures may be described as being open structures (e.g., not enclosed).

Each of the waveguide assemblies may further include one or more gated elements 56. Each exemplary waveguide assembly 52, as shown, includes five gated elements 56. It is to be understood that the exemplary waveguide assemblies 52 can included any number of gated elements. For example, an exemplary waveguide assembly 52 may include one or more gated elements 56, two or more gated elements 56, three or more gated elements 56, five or more gated elements 56, ten or more gated elements 56, twenty or more gated elements 56, thirty or more gated elements 56, fifty or more gated elements 56, etc. Further, for example, an exemplary waveguide assembly 52 may include two hundred or less gated elements 56, one hundred or less gated elements 56, sixty or less gated elements 56, fifty or less gated elements 56, thirty or less gated elements 56, twenty or less gated elements 56, ten or less gated elements 56, five or less gated elements 56, etc.

Figure 14:
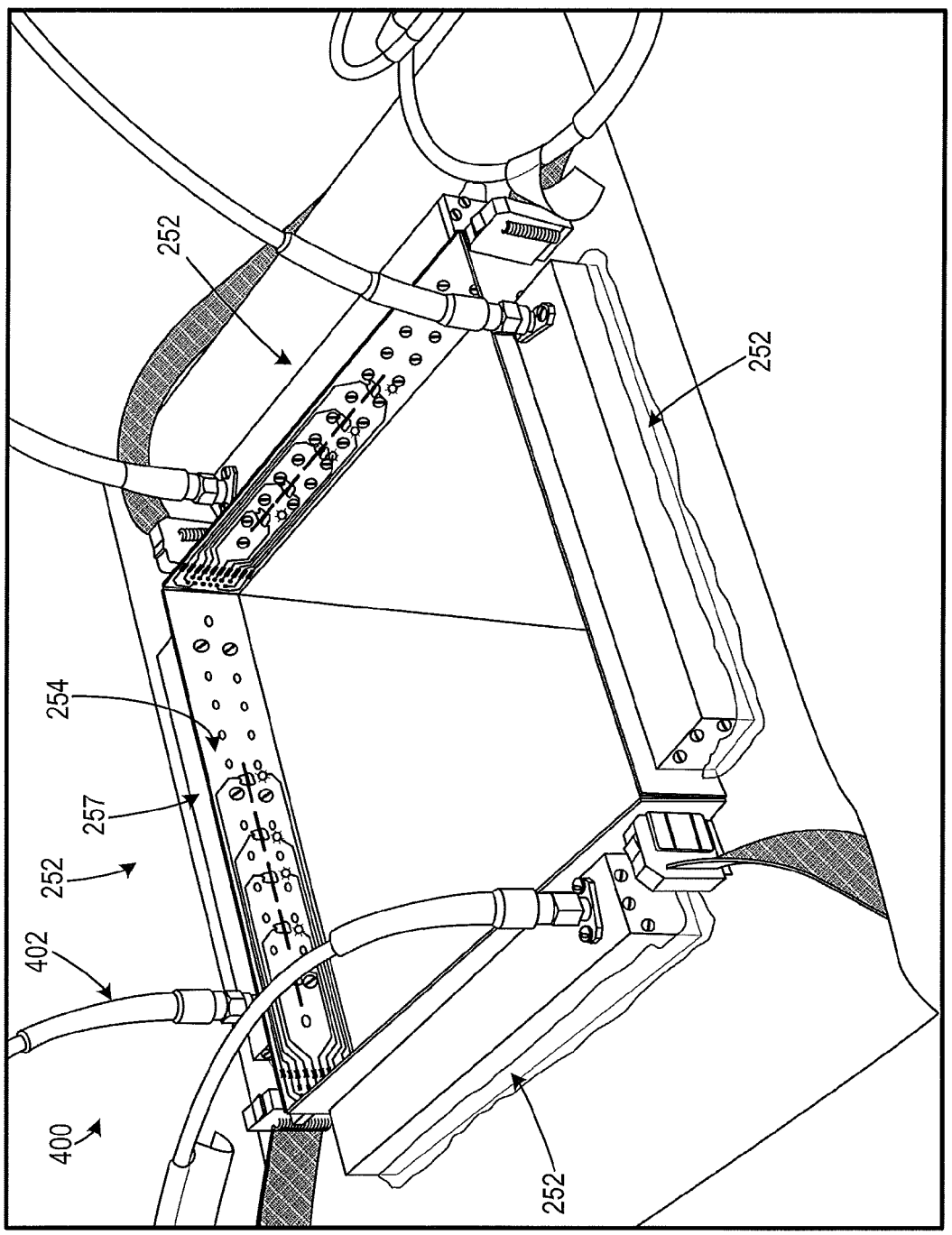
FIG. 14 is a photograph of an exemplary imaging setup using, e.g., the gated elements and waveguide assembly of FIGS. 12-13.
Figure 15:
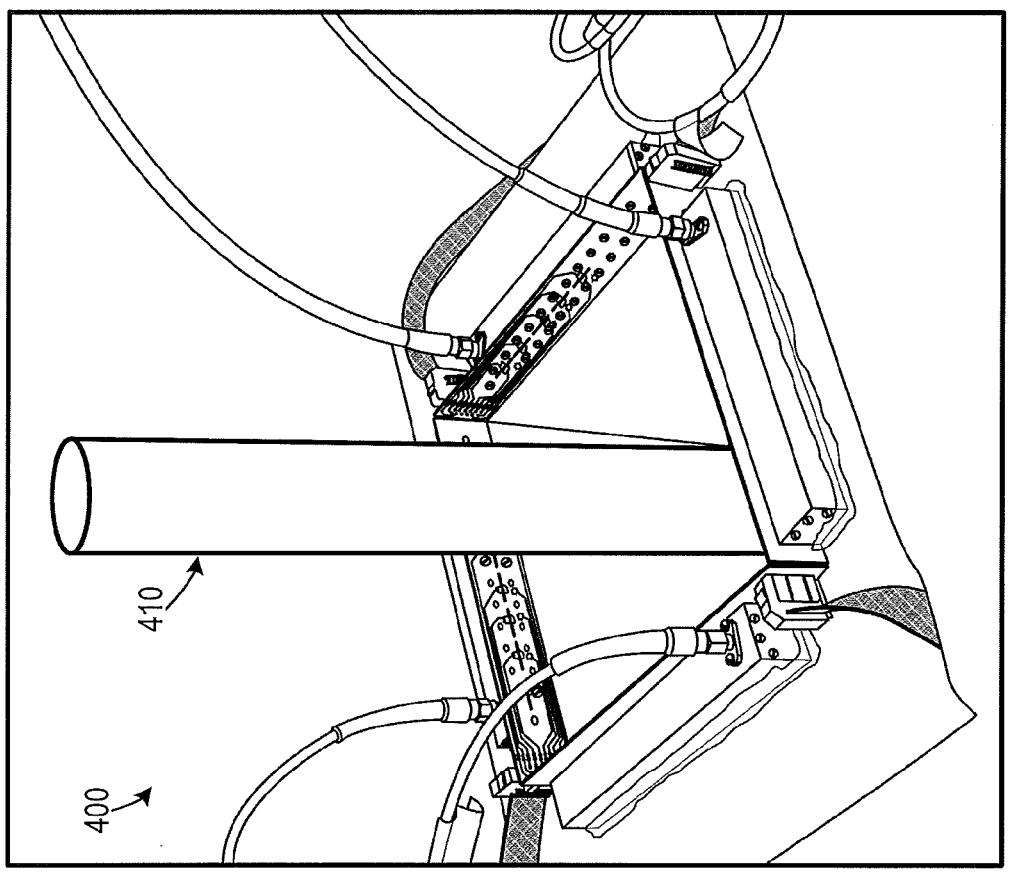
FIG. 15 is a photograph of the exemplary imaging setup of FIG. 14 being used to image a cylindrical object.

The configuration and arrangement of the waveguide assemblies 52 and gated elements 56 may provide two-dimensional and three dimensional imaging of an object of interest located in the imaging domain (e.g., located within the measurement chamber at least partially defined by the waveguide assemblies 52). As shown in FIGS. 2-3, the gated elements 56 may be arranged vertically along each of the waveguide assemblies 52 to provide such three-dimensional imaging capabilities. As shown in FIG. 2 and FIGS. 14-15 described further herein, the waveguide assemblies 52 may be arranged vertically as shown in FIG. 2 or horizontally as shown in FIGS. 14-15 to provide a cylindrical measurement domain 30, or a square measurement domain 30, respectively. Although FIG. 2 and FIGS. 14-15 show two different arrangements, the exemplary waveguide assemblies may be positioned and/or arranged in any configuration capable of providing imaging data (e.g. including angled alignments, slanted alignments, etc.). The cylindrical alignment (e.g., where the waveguide assemblies 52 are vertically oriented around the measurement chamber) as shown in FIG. 2 is suitable for both 3-D and 2-D imaging. The planar alignment as shown in FIG. 14-15 may be more suitable for 2-D imaging. In order to utilize a planar alignment for 3-D imaging, the measurement domain 30 or the OI 10 should move to raster scan different imaging planes.

Each gated element 56 may define an aperture 57 (e.g., opening, etc.) extending into the enclosed volume of the waveguide structure 54. The aperture 57 may allow the gated element to radiate electromagnetic energy when the gated element 56 is used to deliver electromagnetic energy to the object and may perturb electromagnetic energy when the gated element 56 is used to sample the scattered electromagnetic energy. The aperture 57 may have many different shapes and sizes such as, e.g., rectangle, square, triangle, circle, ellipse, tapered geometry and/or a combination thereof. Further, the geometry of the aperture 57 may affect the frequency of operation, polarization, frequency bandwidth, etc.

Each gated element 56 may be configurable in at least a transmission state, a reception state, and a passive state. When in a transmission state, the gated element 56 may be configured to radiate electromagnetic energy. For example, electromagnetic energy may be introduced in the enclose volume of the waveguide structure 54 and may radiate, or emanate, from the gated element configured in the transmission state. It may be described that the gated element is "open" when in the transmission state such that, e.g., electromagnetic energy may radiate, or emanate, therefrom.

When in the reception state, the gated element 56 may be configured to collect, or sample, electromagnetic energy. For example, electromagnetic energy may be received into the enclose volume of the waveguide structure 54 via the gated element configured in the reception state. It may be described that the gated element is "open" when in the reception state such that, e.g., electromagnetic energy may be received therethrough. Additionally, it may be described that the gated element 56 perturbs incoming, or impinging, electromagnetic energy by a modulation frequency based on the MST, which can be later detected by a homodyne receiver (e.g., homodyne receiver 278 of the exemplary system 200 depicted in FIG. 9). The received signal may be then translated to the amplitude and phase of the electromagnetic energy at the location of the gated element 56.

And, when in the passive state, the gated element 56 may be configured to neither radiate nor collect electromagnetic energy. For example, the gated element 56, when in the passive state, may act like any other part or portion of the measurement, or imaging, chamber. In other words, the gated element 56, when in the passive state, may blend in, or be concealed, with the remainder of the measurement chamber by keeping the gated element 56 "closed." The closed state may not allow any radiation of the electromagnetic energy to/from the gated element 56.

Figures 4A, 4B:
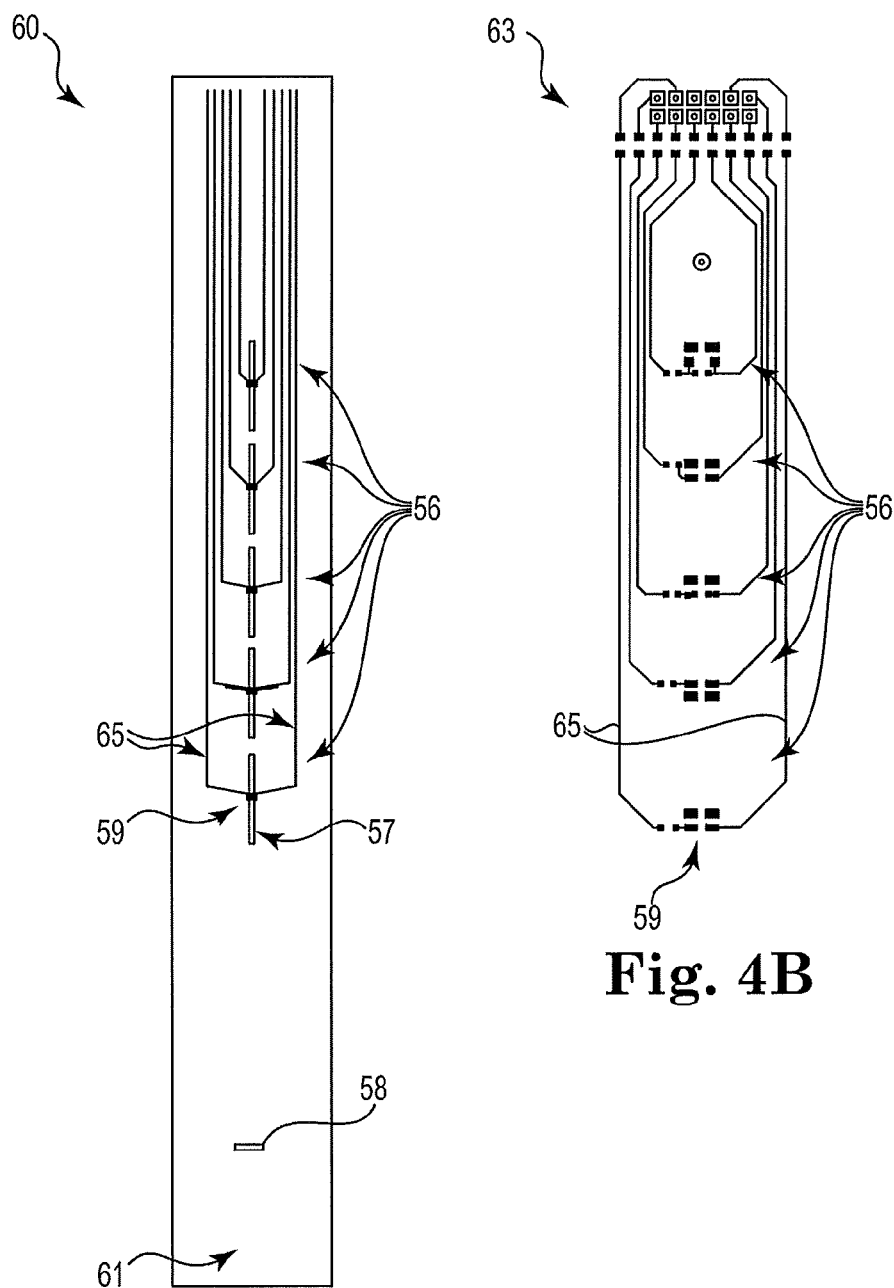
FIG. 4A is a plan view of an exemplary gated element portion of the exemplary waveguide assembly of FIGS. 3A-3B.
FIG. 4B is a circuit diagram of an exemplary gated element portion of the exemplary waveguide assembly of FIGS. 3A-3B.

To provide the states of the gated elements 56, each gated element 56 may include one or more switchable segments 59 (such as, e.g., a p-i-n diode) as shown in FIGS. 4A-4B configurable between a conducting (e.g., low impedance) configuration and a non-conducting (e.g., high impedance)

configuration. To configure the gated element 56 in the passive state, the switchable segment 59 may be configured in the conducting configuration. To configure the gated element 56 in the transmission state, the switchable segment 59 may be configured in the non-conducting configuration. To configure the gated element 56 in the reception state, a modulation signal (e.g., a square wave, etc.) may be applied to the switchable segment 59, which places the switchable segment 59 in the conducting configuration and the non-conducting configuration according to the modulation signal. The modulation signal may further identify, or tag, the electromagnetic energy at the gated element's 56 location.

To place the switchable segments 59 in conducting or non-conducting configurations, the switchable segments 59 may be electrically biased in opposing direction. For example, the switchable segment 59 may be biased in a forward direction to be placed, or configured, into the conducting configuration and may be biased in a reverse direction to be placed, or configured, into the non-conducting configuration. To bias the switchable segments 59, a pair of conductors 65 may extend from biasing circuitry, a controller, etc. to control (e.g., bias, modulate, etc.) the gated elements 56.

As described herein, when a gated element 56 is configured in the reception state, a modulation signal may be applied to the gated element 56 via the conductors 65 to the switchable segments 59, which "tags" the incoming electromagnetic energy at the gated element 56 location. The tagging and modulation may, e.g., increase the sensitivity of the gated element 56, to identify the gated element 56, etc. The modulation signal may have a lower (e.g., significantly lower) frequency than the electromagnetic energy delivered using at least one waveguide assembly of the plurality of waveguide assemblies to irradiate the object of interest. For example, the modulation signal may have a frequency of about 1 hertz, about 1 kilohertz, about 100 kilohertz, about 1 megahertz or more, etc. while the radiation frequency may be frequency of about 100 megahertz, about 1 gigahertz, about 3 gigahertz, about 10 gigahertz, etc. Additionally, each gated element 56, when configured in the reception state, may have or utilize a different modulation signal such that each gated element 56 may be identified by its modulation frequency.

As shown in FIG. 4A, the gated element portion 60 may be a printed circuit board 61. The switchable segments 59 (e.g., p-i-n diodes) may be coupled (e.g., soldered, etc.) to the printed circuit board 61 and conductors 65 may be traces over the printed circuit board. A circuit diagram 63 of the printed circuit board 61 is depicted in FIG. 4B (although the gated elements 56 and the switchable segments 59 are labeled in FIG. 4B, it is to be understood that FIG. 4B depicts only depicts the circuit diagram 63, and thus, the labels of the gating elements 56 and the switchable segments 59 merely point to where the gated elements 56 and switchable segments 59 would be located within the circuit diagram 63).

In one or more embodiments, the aperture 57 of each gated element 56 may define a slot (e.g., an aperture that defines a length that is greater than its width, an aperture that defines a length that is greater than ten times its width, etc.). The slot may have, or define, a length that is half the wavelength of the electromagnetic energy delivered by the plurality of waveguide assemblies 52 to irradiate the object to interest. It is to be understood that the aperture 57 may be any shape or size depending on the frequencies, polarizations, bandwidth of frequencies, etc. to be used in the exemplary imaging system.

As described herein and shown in FIGS. 3A-3B, the waveguide assemblies 52 may include a waveguide structure 54 that defines an enclosed volume. The waveguide structure 54 may include one or more portions. For example, the waveguide structure 54 may include a conductive wall portion 70 and a gated element portion 60. The conductive wall portion 70 may include one or more conductive materials such as e.g., aluminum, copper, steel, brass, etc. and may define one or more walls of the enclosed volume. The conductive wall portion 70 may further define an opening and the gated element portion 60 may be positioned over the opening to enclose the enclosed volume of the waveguide assembly 52.

Further, as described herein, exemplary waveguide structures may not define an enclose volume, and in such embodiments, the one or more portions may not be coupled together to define an enclosed volume. For example, a waveguide structure may include a wall portion and a gate element portion 60 that when coupled together do not define an enclosed volume (e.g., an unenclosed volume, an open volume, a partially-enclosed volume, etc.) but may still be configured to direct, or guide, electromagnetic energy for using in imaging as described herein (e.g., for delivering electromagnetic energy, for collecting electromagnetic energy, etc.).

The gated element portion 60 as shown in FIGS. 4A-4B may define a front surface and a rear surface opposite the front surface. The rear surface may be adjacent to at least a portion of the conductive wall portion 70. The gated element portion 60 may include a conductive layer 62 (e.g., which may define the rear surface) that is conductively coupled to the conductive wall portion 70 and/or one or more dielectric layers to, e.g., to reduce the mismatch between the radiating aperture and the matching fluid or the OI. In at least one embodiment, it may be described that the rear surface of the gated element portion 70 may be conductive and conductively coupled to the conductive wall portion 70. The conductive layer 62 may be described as a "ground" plane or layer.

The waveguide assemblies 52 may further include a fluid gate 58 configured to allow fluid (e.g., matching fluid) to flow into and out of the enclosed volume. As shown, the fluid gate 58 may be defined through gated element portion 60. The fluid gate 58 may be sized, shaped, and located to avoid interference with the imaging processes and methods (e.g., avoid interference with any electromagnetic energy used in the imaging processes and methods, etc.).

The waveguide assemblies 52 may further include a signal coupler 61 configured to electrically couple the waveguide assemblies 52 to exemplary measurement/computing systems and other apparatus described herein via a signal conductor (e.g., a coaxial cable, a copper conductor, etc.). As described herein, the waveguide assemblies 52 are configured to deliver and sample electromagnetic energy. The signal coupler 61 is configured to transmit the electromagnetic energy to be delivered into the waveguide assembly 52 from a signal conductor and allows the electromagnetic energy to be sampled in the waveguide assembly 52 using the signal conductor. For example, the conductive wall portion 70 may further include, or define, the signal coupler 61. In at least one embodiment, the signal coupler 61 may be a co-axial cable connector. The co-axial cable may include a signal conductor (e.g., a copper wire) and conductive shielding around the conductor. When the co-axial cable is attached, or coupled, to the conductive wall portion 70, the signal conductor may extend into the waveguide assembly 52 (e.g., as shown in FIG. 1) to, e.g., sample the electromagnetic energy therein or deliver electromagnetic energy therein.

Each of the waveguide assemblies 52 may be configured to provide a standing wave within the enclosed volume. In one or more embodiments, to provide the standing wave, a first end portion 72 and a second end portion 74 of the waveguide structure 54 may be configured to provide a shorting boundary condition (e.g. using a conductive surface, conductive pins, etc.) when electromagnetic energy is being delivered and/or received by the waveguide assembly 52. In other embodiments, one or more portions of the waveguide structure 54 may be configured to provide an open boundary condition so long as to provide a standing wave within the enclosed volume when electromagnetic energy is being delivered and/or received by the waveguide assembly 52. In another embodiment, one or more portions of the waveguide structure 54 may be configured to provide a loaded/impedance boundary condition to provide a travelling wave within the enclosed volume when electromagnetic energy is being delivered and/or received by the waveguide assembly 52.

Each of the gated elements 56 may be configured to interact (e.g., collect, transmit, etc.) a selected, or particular, polarization of electromagnetic energy. In some embodiments, all of the gated elements 56 may be configured to interact with the same selected polarization. In other embodiments, some of the gated elements 56 may be configured to interact with a first selected polarization and some of the gated elements 56 may be configured to interact with a second selected polarization that is different than the first selected polarization. In still other embodiments, two or more groups of gated elements 56 may be configured to interact with two or more different selected polarizations, respectively. In at least one embodiment, each gated element 56 may be configured to interact with a different polarization.

Figure 5:
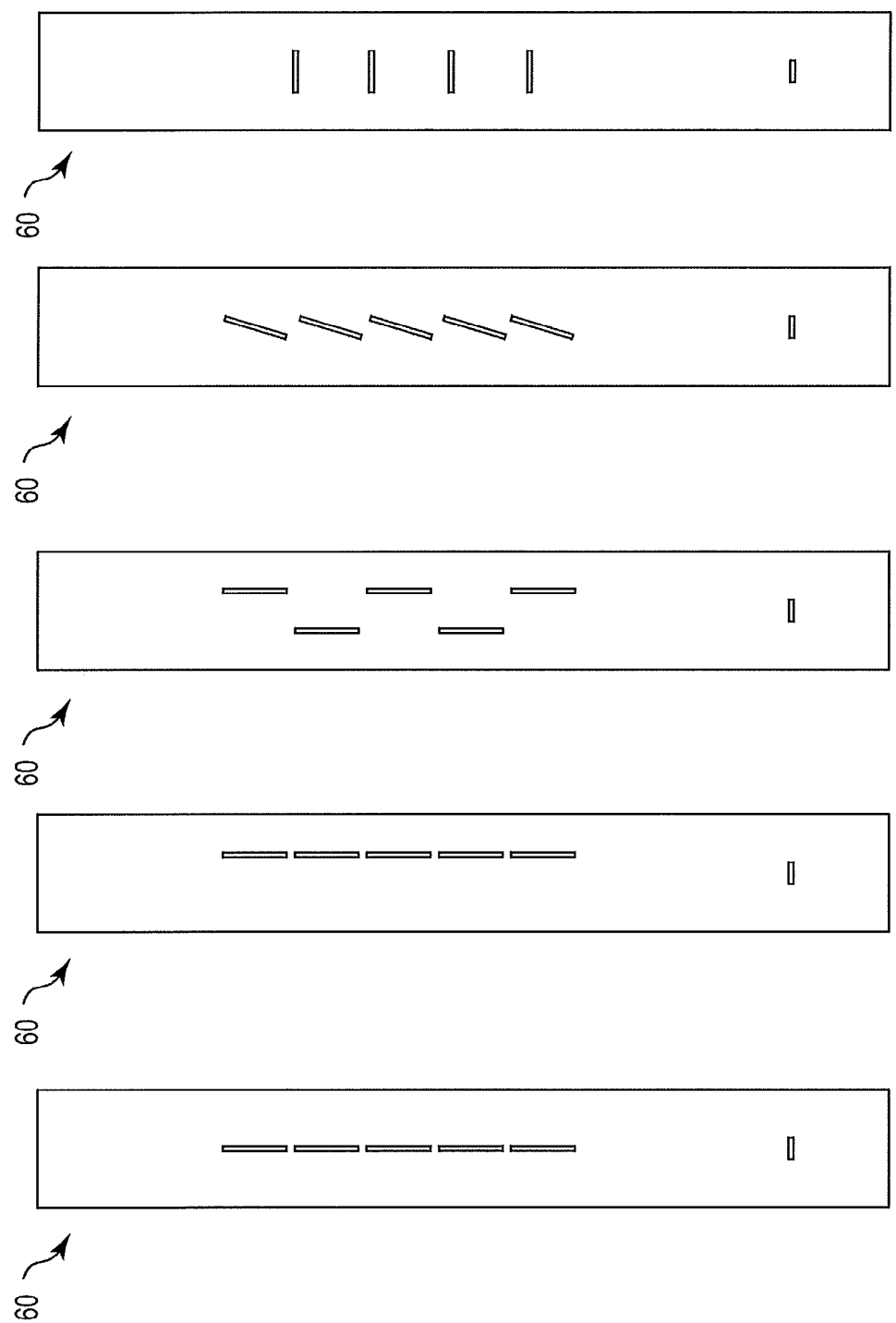
FIG. 5 is a plan view of exemplary gated element portions including parallel gated elements for use with the exemplary waveguide assembly of FIGS. 3A-3B.

Five different gated element portions 60 are depicted in FIG. 5, each having gated elements 56 configured differently. Although the gated elements 56 shown in FIG. 5 are configured differently, each of the gated elements 56 are configured to transmit and/or collect the same polarization because, e.g., each of gated elements 56 are parallel each other.

Figure 6:
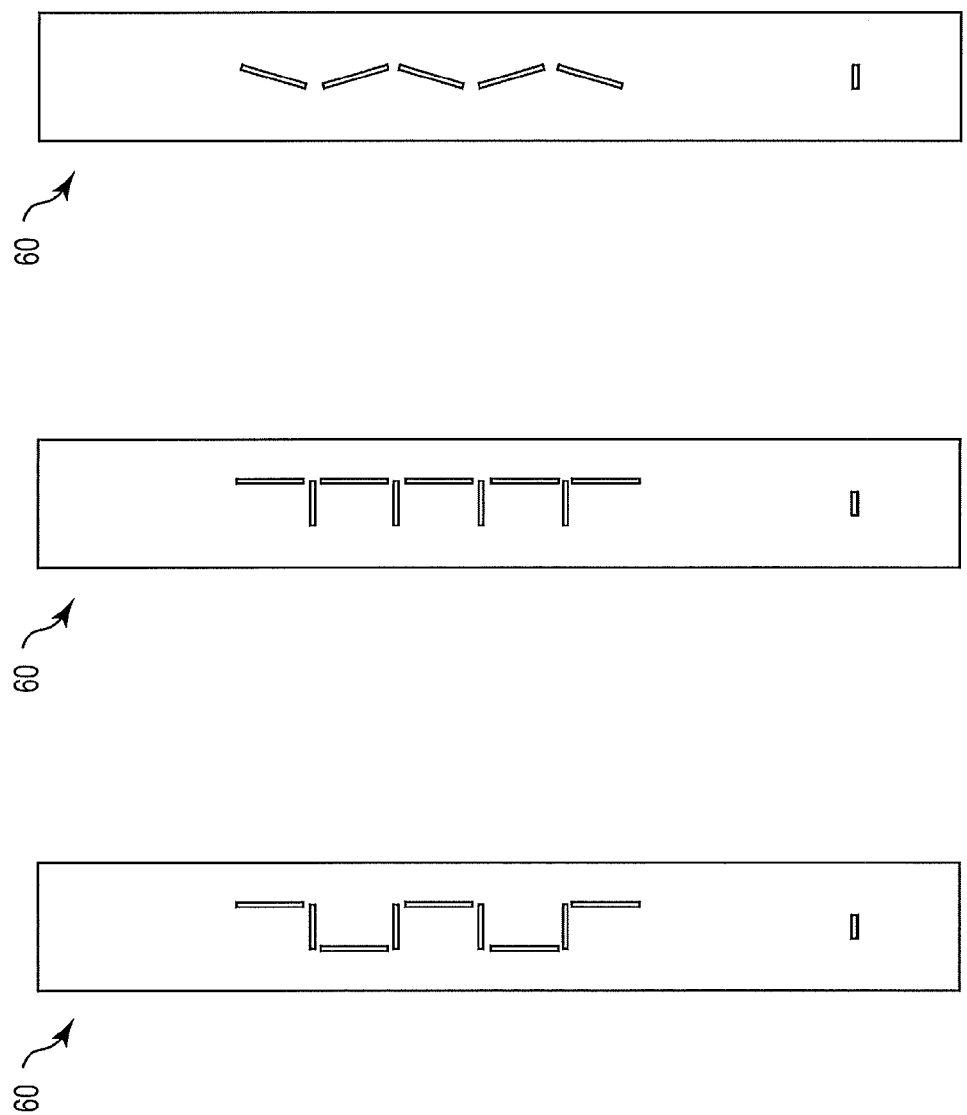
FIG. 6 is a plan view of exemplary gated element portions including non-parallel gated elements for use with the exemplary waveguide assembly of FIGS. 3A-3B.

Three different gated element portions 60 are depicted in FIG. 6, each having a first set of gated elements 56 for transmitting/receiving a first polarization and a second set of gated elements 56 for transmitting/receiving a second polarization that is different that the first polarization. For example, the first polarization may be perpendicular to the second polarization. In at least one embodiment, the first polarization may be vertical and the second polarization may be horizontal. In the rightmost embodiment in FIG. 6, the first set of gated elements 56 has a slant polarization and the second set of gated elements 56 also has a slant polarization that is different than the slant polarization of the first set of gated elements 56.

To establish a baseline measurement for the imaging setup 50, sampling may be performed using each gated element 56 of the one or more waveguide assemblies 52. Such baseline measurements may be used as calibration data, e.g., for comparison to the sampled scattered field collected when using the gated elements 56.

Figure 7:
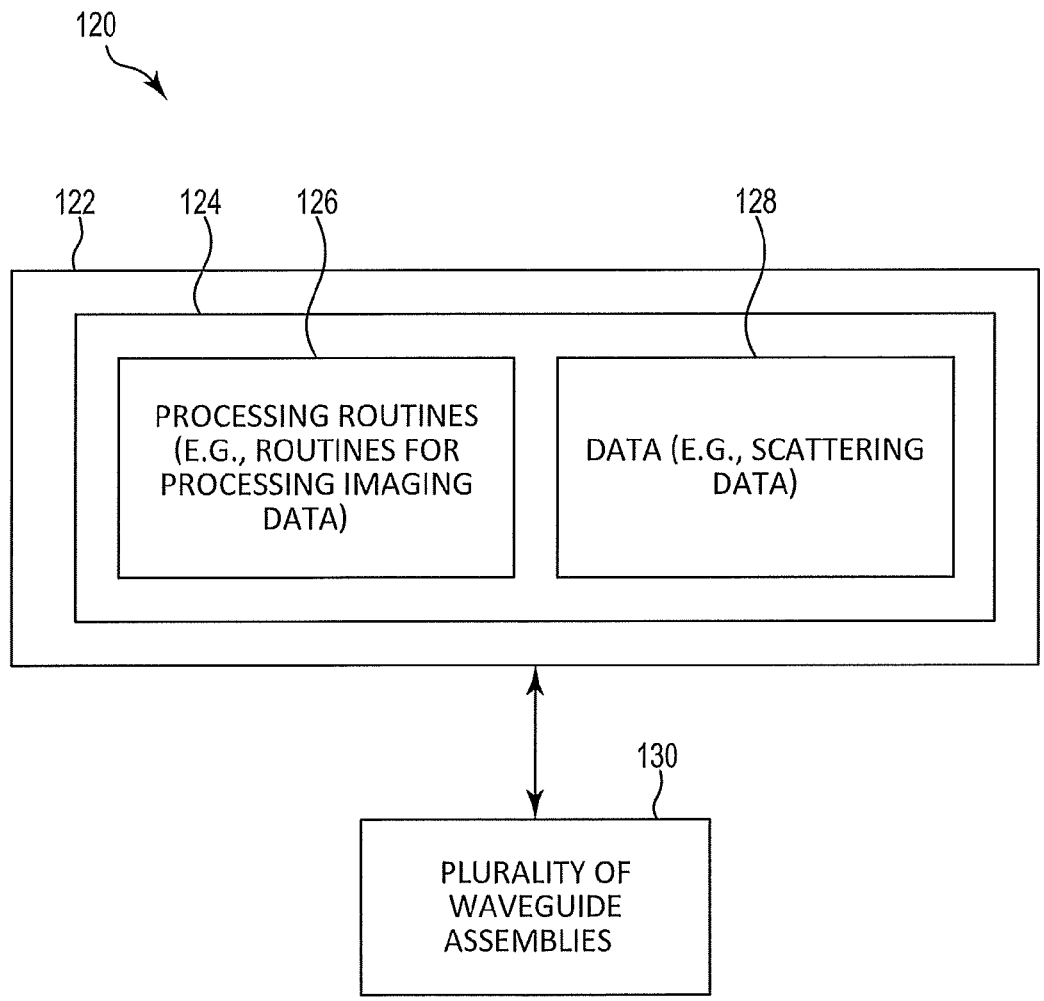
FIG. 7 is a block diagram of an exemplary imaging system, e.g., for use with the imaging setup and apparatus of FIGS. 1-6.

An exemplary imaging system 120 (e.g., a MWI imaging system), e.g., for use with the imaging setup and apparatus of FIGS. 1-6 is depicted in FIG. 7. The system 120 may include processing apparatus 122 and a plurality of waveguide assemblies 130 (e.g., the waveguide assemblies 52 of imaging setup 50). The processing apparatus 122 may be operably coupled to the plurality of waveguide assemblies 130 to facilitate imaging of an object of interest using the waveguide assemblies 130. Generally, the processing apparatus 122 may control the image data acquisition using the plurality of waveguide assemblies 130 and may perform the image reconstruction. More specifically, the processing apparatus 122 may be configured to control and/or initiate the functionality of the plurality of waveguide assemblies 130 for use in imaging an object. For example, the processing apparatus 122 may configure at least one of the gated elements 56 of a waveguide assembly 52 in a transmission state, at least one of the gated elements 56 of a waveguide assembly 52 in a reception state, and the remainder of the gated elements 56 in a passive state.

Further, the processing apparatus 122 includes data storage 124. Data storage 124 allows for access to processing programs or routines 126 and one or more other types of data 128 that may be employed to carry out the exemplary imaging methods. For example, processing programs or routines 126 may include programs or routines for performing computational mathematics, matrix mathematics, compression algorithms (e.g., data compression algorithms), calibration algorithms, image construction algorithms, inversion algorithms, signal processing algorithms, standardization algorithms, comparison algorithms, vector mathematics, or any other processing required to implement one or more embodiments as described herein.

Data 128 may include, for example, sampled electromagnetic energy (e.g., sampled or collected using the plurality of waveguide assemblies 130 in the absence of any object, thereby collecting the incident field, or using a calibration object) including the amplitude and/or phase, data representative of measurements (e.g., electromagnetic scattering data), information on the location and polarity of the collected data, results from one or more processing programs or routines employed according to the disclosure herein (e.g., reconstructed images of an object of interest), or any other data that may be necessary for carrying out the one or more processes or methods described herein.

In one or more embodiments, the system 120 may be implemented using one or more computer programs executed on programmable computers, such as computers that include, for example, processing capabilities (e.g., microcontrollers, programmable logic devices, etc.), data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or processes as described herein or as would be applied in a known fashion.

The program used to implement the processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus for configuring and operating the computer when the suitable device is read for performing the procedures described herein. In other words, at least in one embodiment, the system 120 may be implemented using a computer readable storage medium, configured with a computer program, where the storage medium so configured causes the computer to operate in a specific and predefined manner to perform functions described herein.

Likewise, the imaging system 120 may be configured at a remote site (e.g., an application server) that allows access by one or more users via a remote computer apparatus (e.g., via a web browser), and allows a user to employ the functionality according to the present disclosure (e.g., user accesses a graphical user interface associated with one or more programs to process data).

The processing apparatus 122 may be, for example, any fixed or mobile computer system (e.g., a personal computer or mini computer). The exact configuration of the computing apparatus is not limiting and essentially any device capable of providing suitable computing capabilities and control capabilities (e.g., control the imaging set up configuration and acquire data, such as electromagnetic scattering data) may be used. Further, various peripheral devices, such as a computer display, mouse, keyboard, memory, printer, scanner, etc. are contemplated to be used in combination with the processing apparatus 122.

Further, in one or more embodiments, the output (e.g., an image, image data, incident field data, scattered field data, an image data file, a digital file, a file in user-readable format, etc.) may be analyzed by a user, used by another machine that provides output based thereon, etc.

As described herein, a digital file may be any medium (e.g., volatile or non-volatile memory, a CD-ROM, a punch card, magnetic recordable tape, etc.) containing digital bits (e.g., encoded in binary, binary, etc.) that may be readable and/or writeable by processing apparatus 124 described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing computational mathematics (e.g., matrix inversions, substitutions, Fourier transform techniques, etc.) to reconstruct the images described herein (e.g., from sampled electromagnetic scattering data).

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

One will recognize that a graphical user interface may be used in conjunction with the embodiments described herein. The user interface may provide various features allowing for user input thereto, change of input, importation or exportation of files, or any other features that may be generally suitable for use with the processes described herein. For example, the user interface may allow default values to be used or may require entry of certain values, limits, threshold values, or other pertinent information.

The methods described in this disclosure, including those attributed to the systems, or various constituent components, may be implemented, at least in part, in hardware, software, firmware, or any combination thereof. For example, various aspects of the techniques may be implemented within one or more processors, including one or more microprocessors, DSPs, ASICs, FPGAs, CPLDs, microcontrollers, or any other equivalent integrated or discrete logic circuitry, as well as any combinations of such components, image processing devices, or other devices. The term "processing apparatus," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described components may be implemented together or separately as discrete but interoperable logic devices. Depiction of different features, e.g., using block diagrams, etc., is intended to highlight different functional aspects and does not necessarily imply that such features must be realized by separate hardware or software components. Rather, functionality may be performed by separate hardware or software components, or integrated within common or separate hardware or software components.

When implemented in software, the functionality ascribed to the systems, devices and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

In one or more embodiments, the exemplary system 120 may further include a gated element driver circuit operably coupled between the plurality of waveguide assemblies 130 and the processing apparatus 122. The gated element driver circuit may be used to place each gated element in the appropriate state for imaging. In at least one embodiment, the gated element driver circuit may be connected via USB connection to the processing apparatus 122. Further, the connection of the gated element driver circuit unit and the gated elements may be established using a pair of biasing wires for each gated element. The exemplary system 120 may further include a measurement chamber containing the plurality of waveguide assemblies 130.

In one or more embodiments, the exemplary system 120 may further include a Vector Network Analyzer (VNA) unit or a coherent detection unit (e.g., implementing a modulation scheme) employed to capture the signals received by the plurality of waveguide assemblies 130 for the processing apparatus 122. Due to the presence of the waveguide assemblies, an RF multiplexer unit may be employed by the system 120 to connect the plurality of waveguide assemblies 130 to the VNA unit. The connections between the RF multiplexer and the VNA and the RF multiplexer to the plurality of waveguide assemblies 130 may be established by RF cables. In at least one embodiment, the processing apparatus 122 may be connected to the VNA and the RF multiplexer via General Purpose Interface Bus (GPIB) connections.

Figure 8:
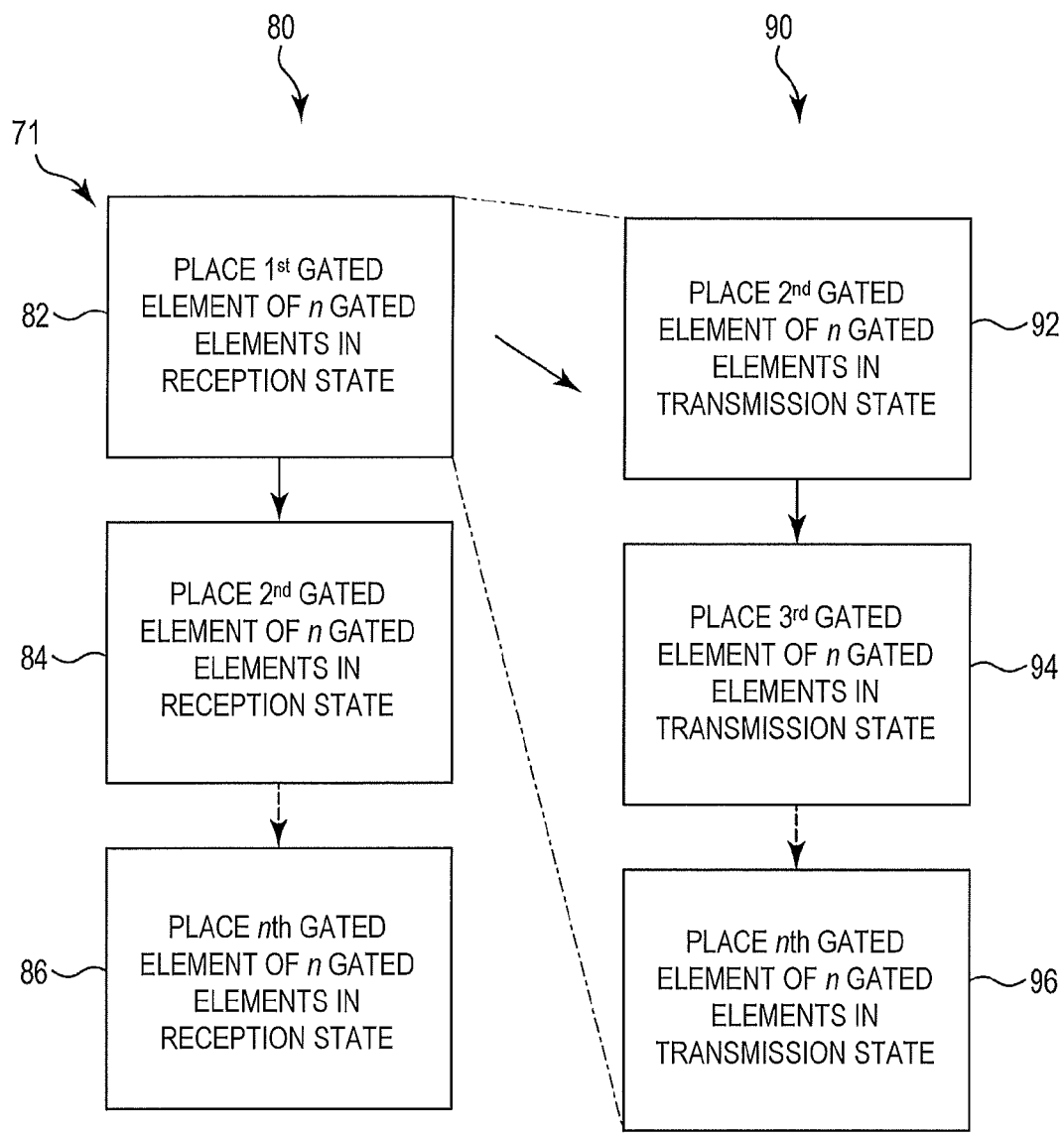
FIG. 8 is a flow diagram for an exemplary imaging method, e.g., for use with the imaging setup of FIG. 7.

An exemplary method 71 of imaging using the system of FIG. 1 is depicted in FIG. 8. The exemplary method 71 includes configuring each gated element individually in the reception state 80 for collecting, or sampling, electromagnetic energy from a scattered electromagnetic field using each gated element and configuring each gated element individually in the transmission state 90 for delivering electromagnetic to irradiate an object of interest resulting in a scattered field using each gated element. The waveguide assembly including the gated element in the reception state may be used to sample the scattered field while the waveguide assembly including the gated element in the transmission state may be used to deliver the electromagnetic energy to the object of interest One gated element may be configured in the reception state to sample, or collect, the electromagnetic energy to be delivered by each of the waveguide assemblies while the remaining gated elements are configured in the passive state except for the one or more gated elements configured in the transmission state. As such, as shown in FIG. 8, a first gated element of n gated elements may be configured in the reception state 82, and then a second gated element of n gated elements may be configured in the reception state 84. The method 71 may continue by configuring each gated element of n gated elements in the reception state until the n-th gated element has been configured into the reception state 86 individually.

For each gated element configured in the reception state 80, electromagnetic energy may be delivered using each gated element of n gated elements to irradiate the object of interest resulting in scattered electromagnetic energy or a scattered field 90. The electromagnetic energy may be delivered using a gated element or a combination of gated elements (and waveguide assemblies). In the embodiment depicted in FIG. 8, one gated element may be configured individually to deliver electromagnetic energy to the object one at a time, or sequentially, until each of the gated elements has individually delivered electromagnetic energy to the object (e.g., each of the gated elements may sequentially deliver electromagnetic energy to the object). For example, a 2nd gated element of n gated elements may deliver electromagnetic energy to the object 92 for the first gated element of n gated elements being configured in the reception state (e.g., active state) 82, and then a third gated element of n gated elements may deliver electromagnetic energy to the object 94 for the first gated element of n gated elements being configured in the reception stated (e.g., an active state) 82. The method 71 may continue delivering electromagnetic energy with each gated element of n gated elements until the n-th gated element has delivered electromagnetic energy to the object 96 for the first gated element of n gated elements being configured in the reception stated (e.g., an active state) 82.

Using the exemplary method 71 depicted in FIG. 8, many scattered field data sets, or imaging data sets, may be gathered for each gated element from multiple different angles. Such data sets may be used to reconstruct an image of the object.

As described herein, although the method 71 delivers electromagnetic energy using a single gated element at a time, or individually, the exemplary methods and/or systems described herein may deliver electromagnetic energy using more than one gated element. For example, multiple combinations of gated elements and/or multiple waveguide assemblies may be used to deliver electromagnetic energy to the object to provide additional scattered field data. Likewise, although the exemplary method 71 samples electromagnetic energy using a single gated element at a time, or individually, the exemplary methods and/or systems described herein may sample electromagnetic energy using more than one gated element and/or waveguide assembly. In essence, different unique combinations of gated elements and/or waveguide assemblies may be used to deliver and/or sample electromagnetic energy.

As described herein, the exemplary system 50 may use gated elements 56 and the waveguide assemblies 52 to deliver electromagnetic energy to (e.g., to illuminate) the OI 10 from multiple different angles and to sample the resultant scattered field from multiple different angles. The data gathered may then be processed using a processing apparatus to reconstruct a quantitative image of the OI 10 in an imaging domain 32. As used herein, a "quantitative" image may be defined as an image that includes data that is calibrated to directly relate to an actual property such as dielectric permittivity and/or magnetic permeability. For instance, a person having skill in the art may determine the permittivity and/or permeability of a particular location in an object based on the quantitative image. In other words, the data in a quantitative image is not data that is merely relative to itself.

Implementing such a data-collection apparatus within a microwave imaging (MWI) system for generating quantitative images may allow for many possible diversities of field interrogation and measurement the use of multiple frequencies, the collection of substantial amounts of scattering data at the multitude of gated element locations, the use and measurement of arbitrary polarizations (without any need for mechanical rotation for fast data acquisition), and the use of a multitude of transmitter locations to introduce a multitude of incident fields upon the OI 10.

EXEMPLARY SYSTEM

Figure 9:
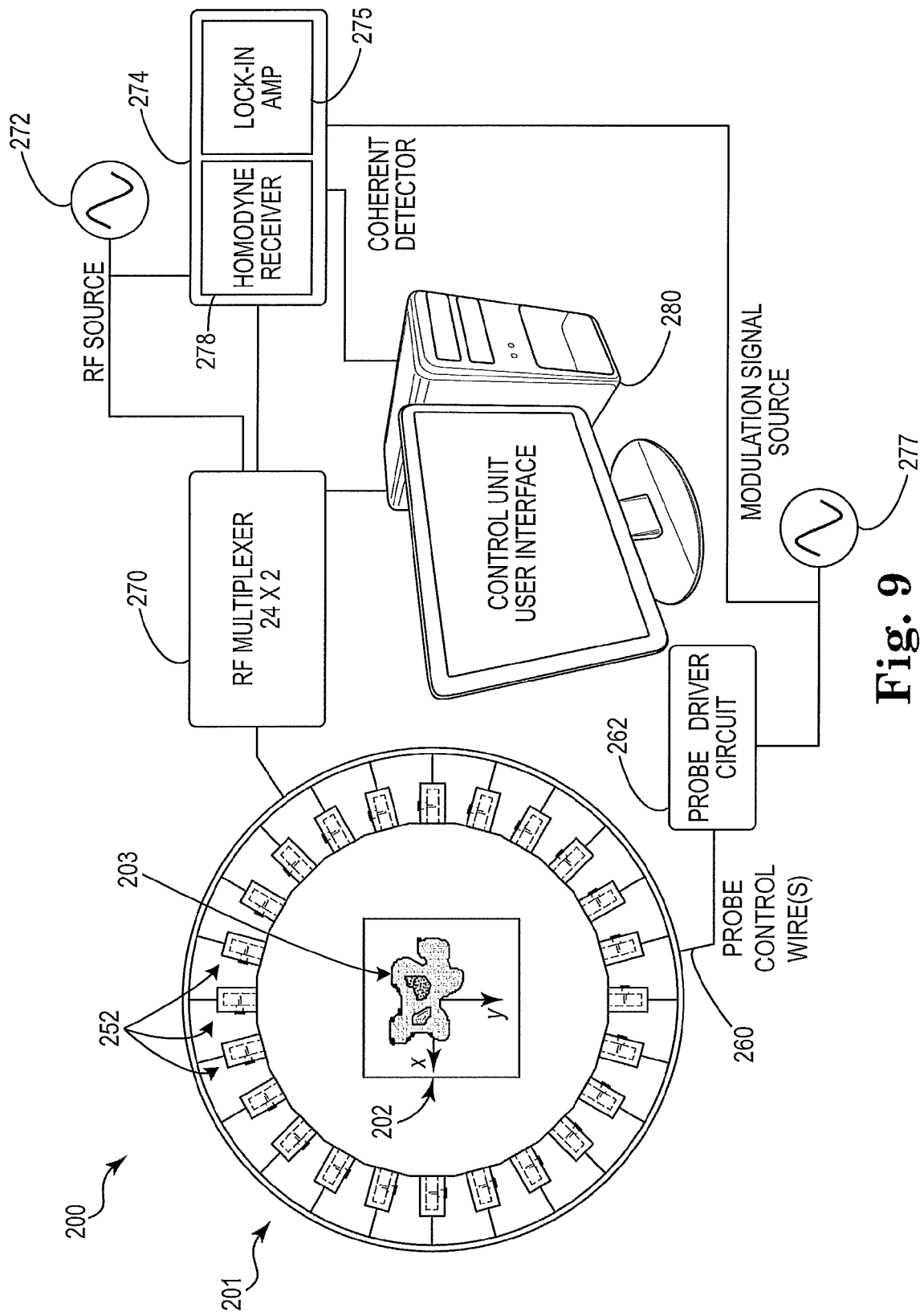
FIG. 9 depicts an exemplary imaging system.

An exemplary single polarized system is described herein with reference to FIGS. 9-17. A schematic representation of an exemplary MWI system 200 is shown in FIG. 9. The exemplary system 200 includes an imaging setup 201 similar to the imaging setup 50 and apparatus described herein with reference to FIGS. 1-6. As shown, the imaging setup 201 is configured to image an object of interest (OI) 203 in the imaging domain 202.

Figure 12:
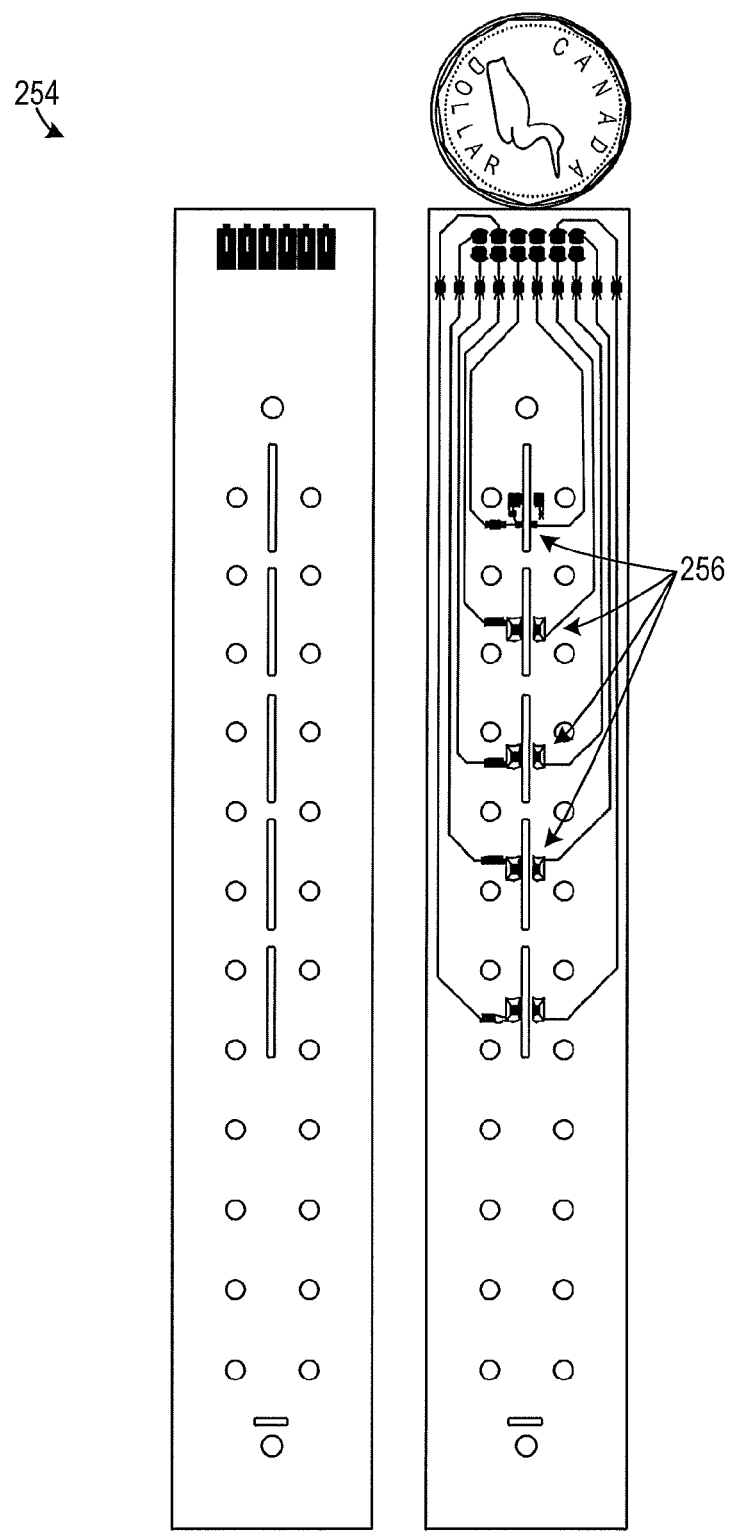
FIG. 12 is a photograph of an exemplary gated element portion.
Figure 13:
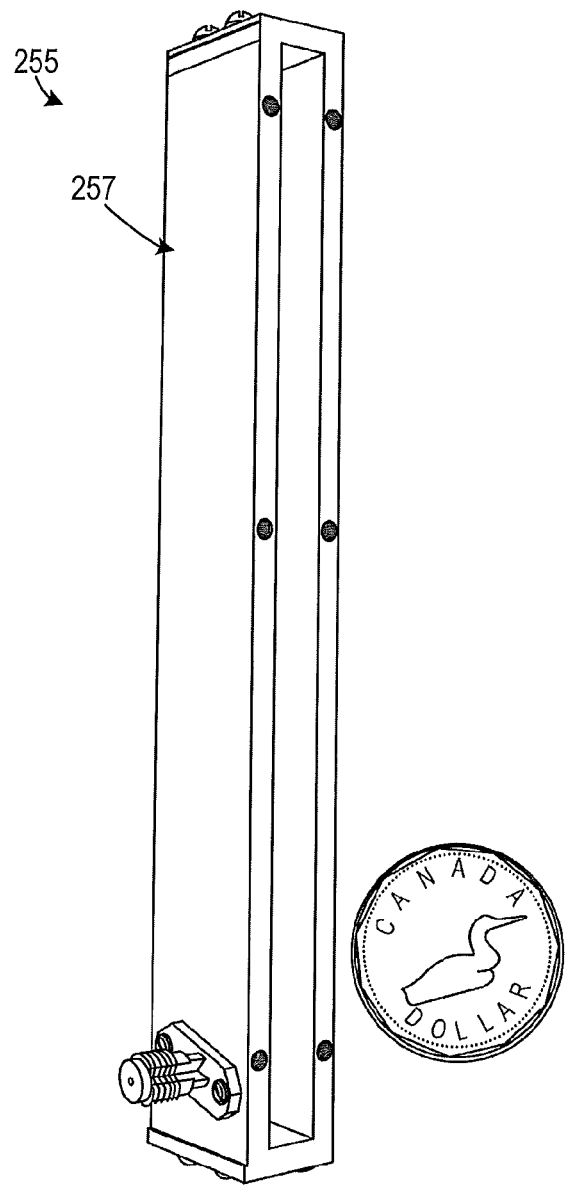
FIG. 13 is a photograph of a portion of an exemplary waveguide assembly.

The exemplary imaging setup 201 includes twenty-four rectangular waveguide assemblies 252, each including a waveguide structure 255 that includes a wall portion 257 and a gated element portion 254. The wall portion 257 may include (e.g., is manufactured from, formed of, etc.) metallic conductors such as aluminum, copper, brass or other metals and define at least three edges as shown in FIG. 13 (loonie provided for scale). The gated element portion 254, e.g., a printed circuit board (PCB), may define a fourth edge as shown in FIG. 12 (loonie provided for scale). The gated element portion 254 may include of a conductive 'ground' layer which sits on (e.g., is adjacent to, is in contact with, etc.) the wall portion 257. The waveguide structure 255 and the gated element portion 254 may be described as forming a closed-chain chamber, here a 24-edge polygon, around the OI 203.

Each PCB may include a plurality of gated elements 256 as shown in FIG. 12. Each gated element 256 may include a slot with a p-i-n diode located in slot's center that is connected to a pair of biasing wires. The p-i-n diodes may be utilized to control the operation of the gated elements 256 and may be coupled via probe control wire(s) 260 to and controlled through a driver circuit 262, which biases or unbiases the gated elements. If a gated element 256 is biased, its p-i-n diode is "on" or "shorted" (further, e.g., "conducting" or "low impedance"). If a gated element 256 is unbiased, its p-i-n diode is "off" or "opened" (further, e.g., "nonconductive" or "high impedance"). The driver circuit 262 may be referred to as the "gated elements driver-circuit." The routing of the biasing wires 260 may be chosen on the opposite layer of the gated element portion 254 (e.g., PCB) with respect to the waveguide structures 255. The biasing wires 260 may be configured so as to not perturb the electromagnetic field collection because of the wires 260 are shielded by the PCB ground layer located on the opposite side of the gated element portion 254. Further, the biasing wires 260 may not perturb the scattered field from the OI 203 because of the biasing wires 260 may be located adjacent, and sufficiently close, to the PCB ground layer of the gate element portion 254. Finally, the waveguide assemblies 252 may be connected to a 24-to-2 RF multiplexer/switch 270 that is followed by a signal generator (e.g., a RF source) 272 and a sensitive coherent receiver 274. The RF switch 270 may be configured to enable each waveguide assembly 252 to either deliver RF energy to its gated elements 256 or to collect the RF energy from its gated elements 256.

The imaging domain 202, D, where the complex dielectric profile of the OI 203 may be reconstructed. Each waveguide assembly 252 of the system 200 of FIG. 9 can operate in either deliver or collect mode. The former mode, deliver mode, may "deliver" the energy from the RF source 272 to a transmitting gated element 256, which is selected by the element, or probe, driver circuit 262. The latter mode, collect mode, "collects" the energy from a receiver element, which is modulated by the element, or probe, driver circuit 262. The deliver/collect waveguides are selected through the RF switch 270. After selecting a pair of waveguide assemblies 252, the gated element 256 of the delivery waveguide 252 may successively illuminate the OI 203 while the gated elements 256 on the collector waveguide assemblies 252 receive the scattered field, using a modulated scattering technique (MST).

The MST may be based on the fact that the field scattered by a gated element 256 is proportional to the original field at the location of the gated element 256. The collector waveguide assembly 252 thus may be configured to collect a modulated signal that is proportional to the field only at the location of the gated element 256. For each object to be imaged, the following two sets of measurements may be used: a measurement with the presence of the object of interest 203 inside the chamber that is referred to as the $\vec{E}^{tot.}$ or the total-field measurement, and a measurement with the absence of the object 203 that is referred to as the $\vec{E}^{inc}$ or the incident-field measurement. Subtracting the $\vec{E}^{inc}$ from the $\vec{E}^{tot.}$ may result in the scattered field data required by an exemplary imaging algorithm. For an exemplary MST implementation, the gated elements 256 may be successively modulated by a square waveform M(t):

$$M(t) = \frac{V_m}{2} + \frac{2V_m}{\pi}\sin(\omega_m t) + \sum_{n=3,5,\ldots}^{\infty} \frac{2V_m}{n\pi}\sin(n\omega_m t) \quad (1)$$

with amplitude of $V_m$ and fundamental angular frequency of $\omega_m$. The square waveform contains harmonics of $\omega_m$, thus the interaction of the gated element 256 with the electromagnetic field may produce various harmonics at frequencies of $\omega_{RF} \pm n\omega_m$ where n is the harmonic index. Note that the modulation frequency, $f_m$, in this exemplary system 200, is significantly lower than the imaging frequency, $f_{RF}$. While a gated element 256 is modulated, the electromagnetic field will be perturbed at the location of the modulated gated element 256. The perturbed field, modulated at $f_m$, is proportional to the field at the gated element 256 location (e.g., MST principle). In order to obtain the field information, the received signal (containing $\omega_{RF} \pm n\omega_m$) is mixed by the in-phase (I) as well as the quadrature-phase (Q) samples of the original unperturbed RF signal. Note that I and Q only contain the imaging frequency, $f_{RF}$. The output of the mixers, the IF signals, are then precisely measured by a lock-in amplifier 275. The measured data may then be finally translated into the amplitude and phase of the field at the gated element's location (e.g., using the computing apparatus and control unit interface 280 of the exemplary system 200 of FIG. 9).

Figure 10A:
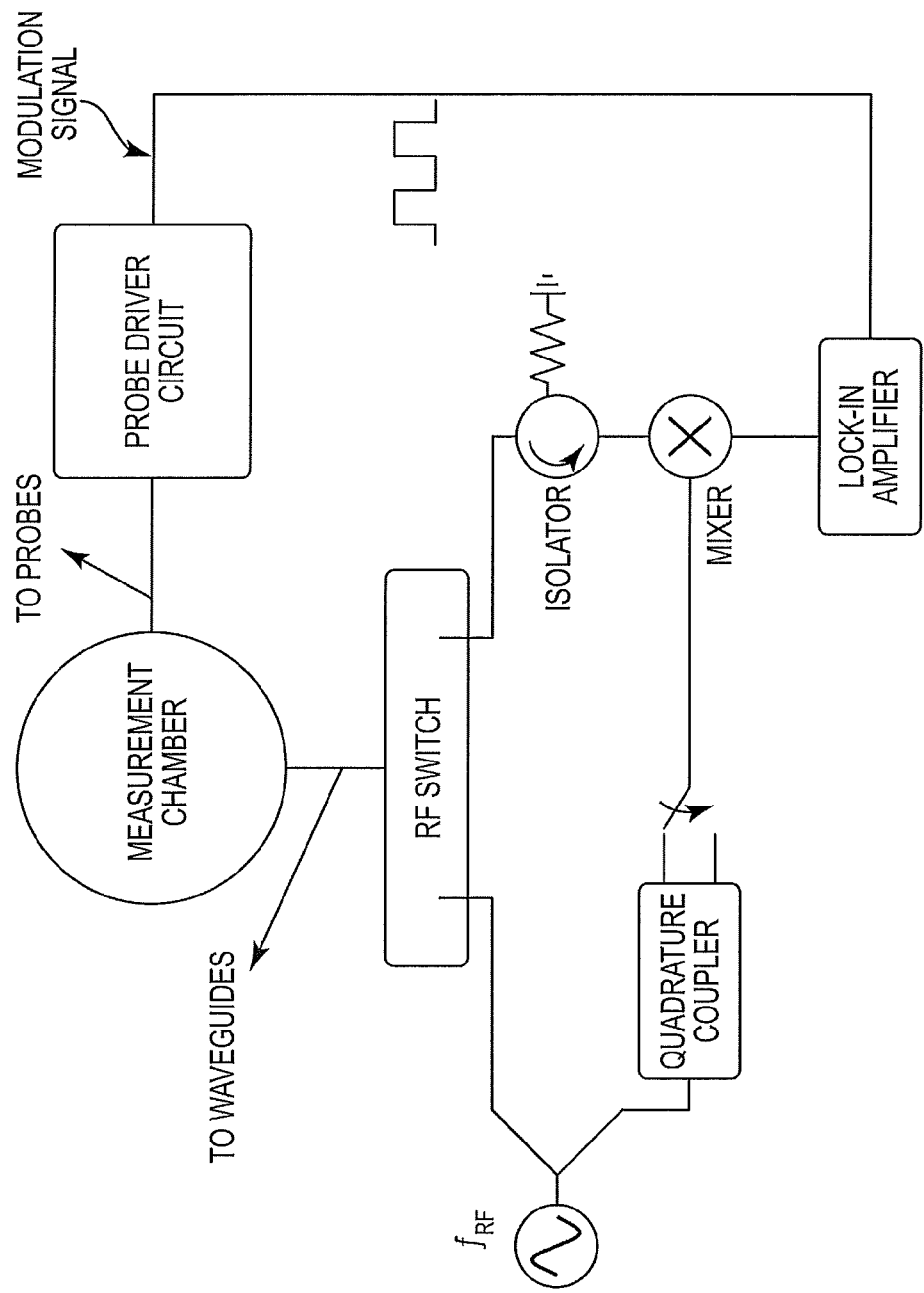
FIGS. 10A-10B depicts exemplary electrical schematics for the imaging system of FIG. 9.
Figure 10B:
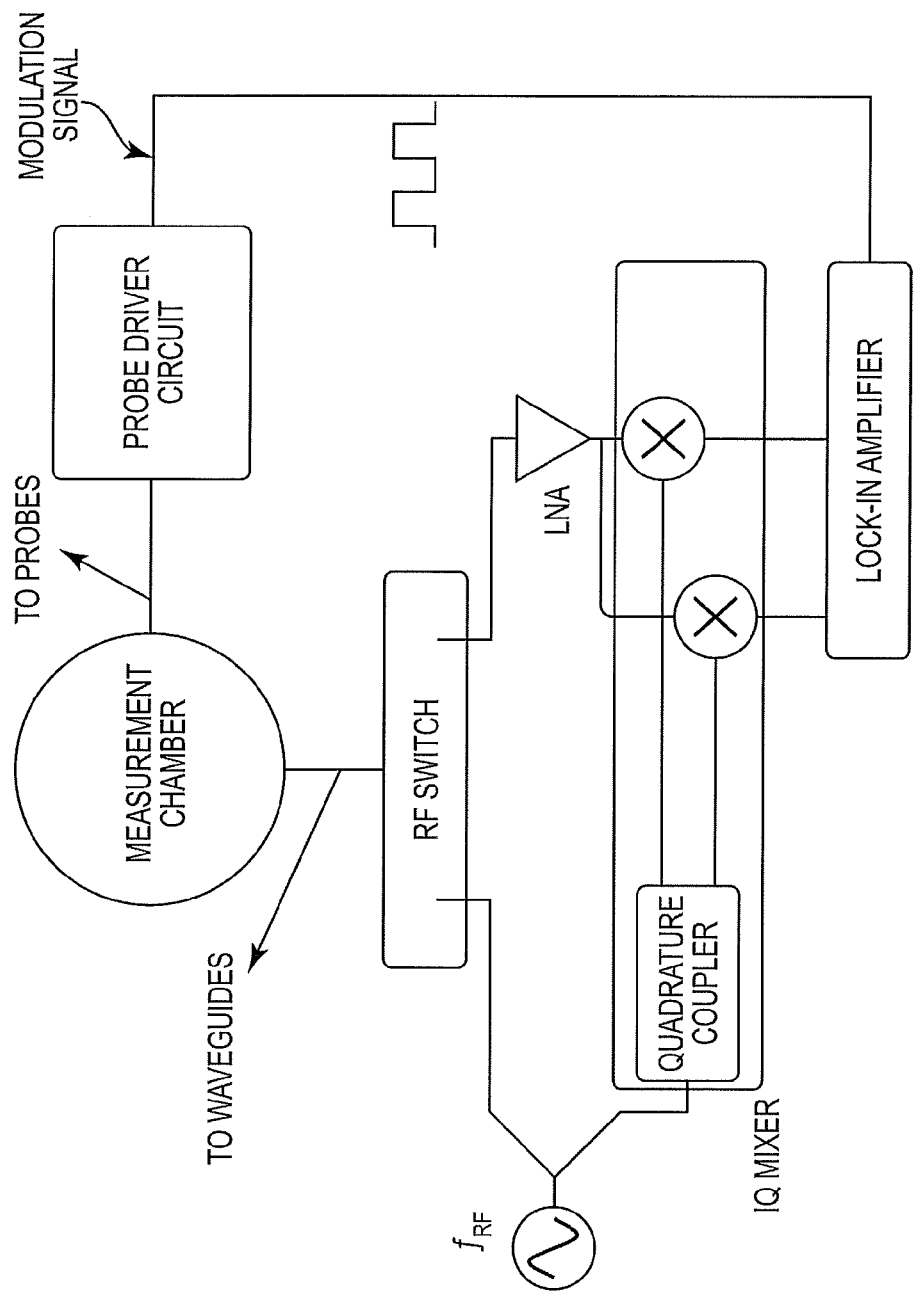
Figure 11:
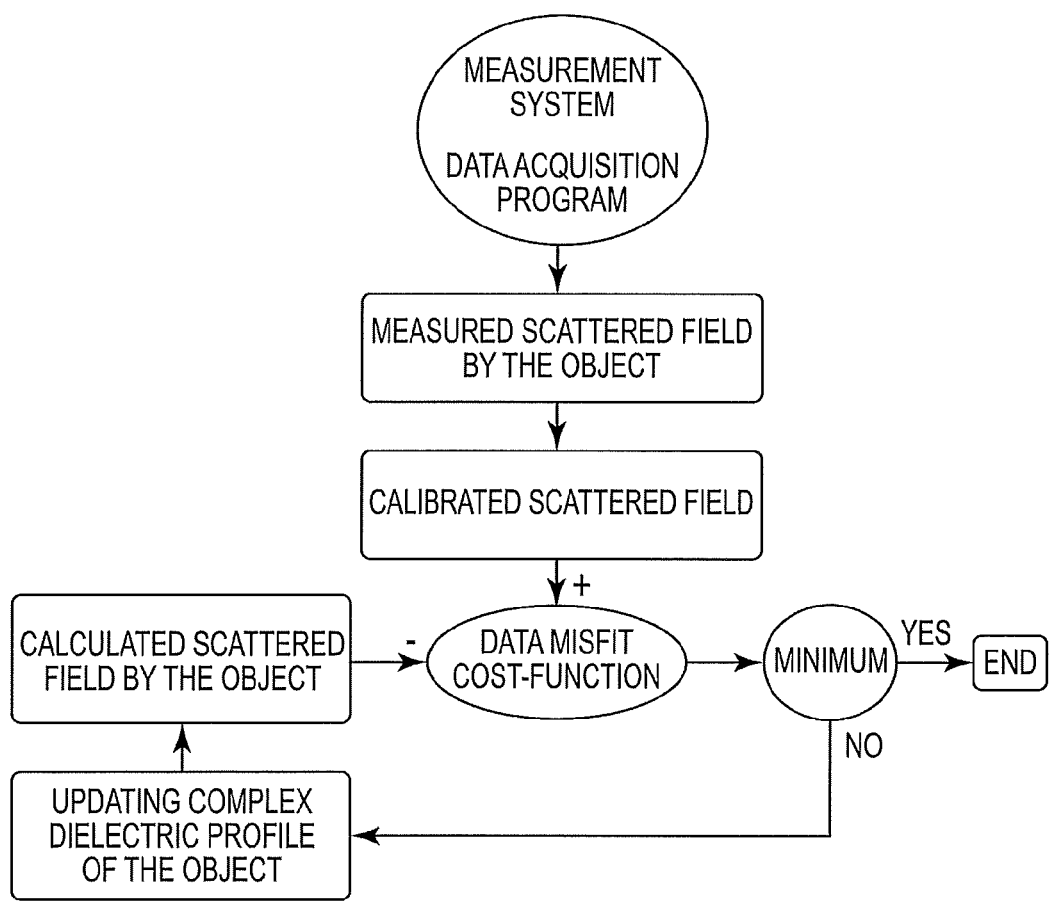
FIG. 11 is a flow diagram for an exemplary imaging method, e.g., for use with the imaging system of FIG. 9.

The aforementioned data collection scheme may be repeated for each transmitter-receiver pair of gated elements 256 until all the data is collected. Two examples of implementing such a receiver for use in the exemplary systems, methods, and apparatus described herein are schematically depicted in FIGS. 10A-10B. The first example schematically depicted in FIG. 10A uses a single mixer, and the second example schematically depicted in FIG. 10B uses an IQ-mixer.

As shown, a 3-D MWI chamber using 24 waveguide assemblies, each consisting of 5 slot gated elements, may be utilized by the imaging system of FIG. 9. The total number of slot gated elements 256 in this example is 24 waveguide assemblies×5 gated elements=120. The gated elements 256 successively illuminate the OI 203 at a frequency of $f_{RF}$, referred to as the imaging frequency, while the remaining gated elements 256 successively collect the field scattered by the OI 203. The gated elements 256 operate in three modes. The first mode is a transmit or transmission mode where the diode is reversed biased ("off") where the diode does not affect the slot, allowing the slot to radiate. By choosing a slot length to resonate at $f_{RF}$, the radiation efficiency increases significantly. In the exemplary system, the length of the slot was set to $\lambda_g/2$, where $\lambda_g$ is the waveguide wavelength.

The second mode is a passive mode where the diode is forward biased ("on") such that the diode shorts the slot in the center of the gated element 256. In the passive mode, the slot cannot radiate and is concealed (e.g., electromagnetically concealed, electromagnetically invisible, etc.) within the metallic ground plane of the PCB of the gated element portion 254.

The third mode is receive mode where the diode is modulated by a modulation square signal, denoted by M(t) (see equation (1)). When in receive mode, the slot gated element 256 may collect the impinging field on the gated element's slot, or aperture, at the modulation frequency of $f_m$. The modulation signal may be provided by a modulation signal source 277 as shown in FIG. 9.

An exemplary waveguide assembly 52, 252 and its gated elements 56, 256 used in the exemplary system of FIG. 9 are shown in FIGS. 3-4 and 12-13. In these embodiments, electromagnetic waves may be confined inside the structure 54, 60, 70, 255, 254 of the waveguide assembly 52, 252, where one or more propagating modes are excited. The excitation of waveguide assemblies 52, 252 depends on the frequency, dimensions, and internal dielectric properties of the structure 54, 60, 70, 255, 254 of the waveguide assembly 52, 252. If a slot is cut into a wall of the structure of the waveguide assembly 52, 252 and the slot perturbs the surface currents flowing on the waveguide walls, the slot will radiate. Due to the presence of the structure in the waveguide assembly 52, 252, the radiation is unidirectional. By changing the structure of the waveguide assembles 52, 252, such as, e.g., the walls, the location of the slots, the walls and/or slots orientations, etc. various polarizations can be obtained such as, e.g., slant, vertical, and horizontal polarizations. The exemplary waveguide assemblies 52, 252 of FIGS. 3-4 and FIG. 12 includes 5 vertically-oriented half-wavelength gated element 56, 256, which are suitable for illuminating/collecting horizontal electric field, $E_\phi$, as well as vertical magnetic field, $H_z$. Note that the highest radiation efficiency can be obtained by setting the slot length to resonant at, e.g., half-wavelength of the electromagnetic energy delivered to the OI 203.

Depending on the application and the dielectric properties of the OI, a mismatch may exist between the OI 203 and the background medium inside the imaging chamber. For instance, the dielectric properties of biological tissues may be substantially different than that of the air, and thus, a matching material may be used for most biomedical applications of MWI. Salt-water solution may have been used for imaging human forearm and bovine leg (see, e.g., M. Ostadrahimi, P. Mojabi, A. Zakaria, J. LoVetri, and L. Shafai, "Enhancement of Gauss-Newton inversion method for biological tissue imaging," Microwave Theory and Techniques, IEEE Transactions on, vol. 61, no. 9, pp. 3424-3434, 2013). The exemplary MWI systems described herein may using imaging chambers that are filled by a matching fluid, e.g., water, glycerin, and oil as well as solid materials, e.g., ceramic, rubber, and carbon-based material. The matching material may be located inside the waveguides to reduce the guided wavelength, which reduces the size of the slots, or inside the imaging chamber, or both. In each case, the effective guided wavelength may be calculated and the dimensions of the slots may be adjusted for radiation efficiency. To provide matching fluid inside and outside the waveguides, a "fluid gate" may be defined in the exemplary waveguide assemblies 52, 252 that may allow liquid flow into and out of the waveguide assemblies 52, 252 and the imaging chamber. In at least one embodiment, the fluid gate may be located in a spot with minimum interference with the data collection.

The goal of a MWI problem may be to reconstruct the relative complex dielectric properties of an OI 203, denoted by $\epsilon_r(\vec{r})$ at position $\vec{r}$ within an imaging domain 202, $\mathcal{D}$, which is shown in FIG. 9. The mathematical optimization problem associated with quantitative MWI may be described as being inherently nonlinear and ill-posed, and thus, different algorithms and regularization techniques may be used treat, or address, these difficulties. For example, for the inverse problem, the OI 203 confined within the imaging domain 202, $\mathcal{D}$, may be considered and surrounded by transmitters and receivers on a measurement surface, denoted by $\mathcal{S}$. The background medium is a homogeneous background with a known complex relative permittivity, $\epsilon_b$. The contrast of the OI 203 is then defined as $$X(\vec{r})=(\epsilon_r(\vec{r})-\epsilon_b)/\epsilon_b \quad (2)$$

where $\epsilon_r(\vec{r})$ is the complex relative permittivity of the OI. Outside the imaging domain 202, $\mathcal{D}$, X=0. The background and OI 203 may be assumed to be non-magnetic, i.e., their relative permeability $\mu_r=1$.

The calibrated data may be inverted using an exemplary contrast source inversion algorithm (CSI) (see, e.g., P. Van Den Berg and R. Kleinman, "A contrast source inversion method," Inverse problems, vol. 13, p. 1607, 1997) formulated using an exemplary finite element method (FEM) (see, e.g., A. Zakaria, C. Gilmore, and J. LoVetri, "Finite-element contrast source inversion method for microwave imaging," Inverse Problems, vol. 26, p. 115010, 2010; and A. Zakaria and J. LoVetri, "The finite-element method contrast source inversion algorithm for 2d transverse electric vectorial problems," Antennas and Propagation, IEEE Transactions on, vol. 60, no. 10, pp. 4757-4765, October 2012) or an exemplary Gauss-Newton inversion method (see, e.g., P. Mojabi, J. LoVetri, and L. Shafai, "A multiplicative regularized gauss-newton inversion for shape and location reconstruction," Antennas and Propagation, IEEE Transactions on, vol. 59, no. 12, pp. 4790-4802, December 2011). Both exemplary algorithms may iteratively update $\epsilon_r(\vec{r})$ until a best match is obtained between the numerically calculated field scattered by the OI 203 with that collected, then calibrated, from the measurement system 200. A flow chart of an exemplary algorithm is presented in FIG. 11.

The exemplary inversion algorithm used by the system 200 may not fully model the measurement system 200, e.g., due to a heavy computational cost. Therefore, data collected from the measurement system 200 may be calibrated. The task of calibrating an imaging system 200 may be highly dependent on the system configuration. Exemplary calibration techniques may, e.g., use the incident-field or use the scattered-field of a known reference object, such as a perfect electric conductor (PEC). Utilizing the scattered-field calibration from a PEC reference object may provide a suitable exemplary calibration method for exemplary imaging systems (see, e.g., M. Ostadrahimi, P. Mojabi, C. Gilmore, A. Zakaria, S. Noghanian, S. Pistorius, and J. LoVetri, "Analysis of incident field modeling and incident/scattered field calibration techniques in microwave tomography," Antennas and Wireless Propagation Letters, IEEE, vol. 10, pp. 900-903, 2011). In a multi-polarized scenario, each polarization may be calibrated separately for each chosen source model.

To calibrate the data, a PEC reference object may be placed inside a measurement chamber. The scattered field produced by this reference object may be collected. For any active transmitter, an individual calibration factor may be defined for each gated element for each frequency of operation. For an active transmitter, the calibration factor at each gated element may be the ratio of the numerically calculated scattered field by the reference object to the measured field of the same object at the gated element's location.

An exemplary, prototype MWI system 400 was manufactured with air as the background medium as shown in FIG. 14. Four rectangular waveguide assemblies 252 including Aluminum wall portions 257 and four gated element portions (e.g., PCBs) 254 with five gated elements were fabricated. The rectangular waveguide assemblies 252 252 were chained horizontally with the gated element structures 254 sitting on the narrow walls of the wall portions 257. The dominant $TE_{10}$ mode was excited by a quarter-wavelength-spaced coaxial connectors 402 at, e.g., 8.1 GHz and 8.3 GHz. Thus, the gated elements illuminate and collect the $E_z$ field. The dimensions of the rectangular aperture of each gated element was 14×1 mm and a p-i-n diode was placed in the center of the rectangular aperture or slot.

Figure 16A:
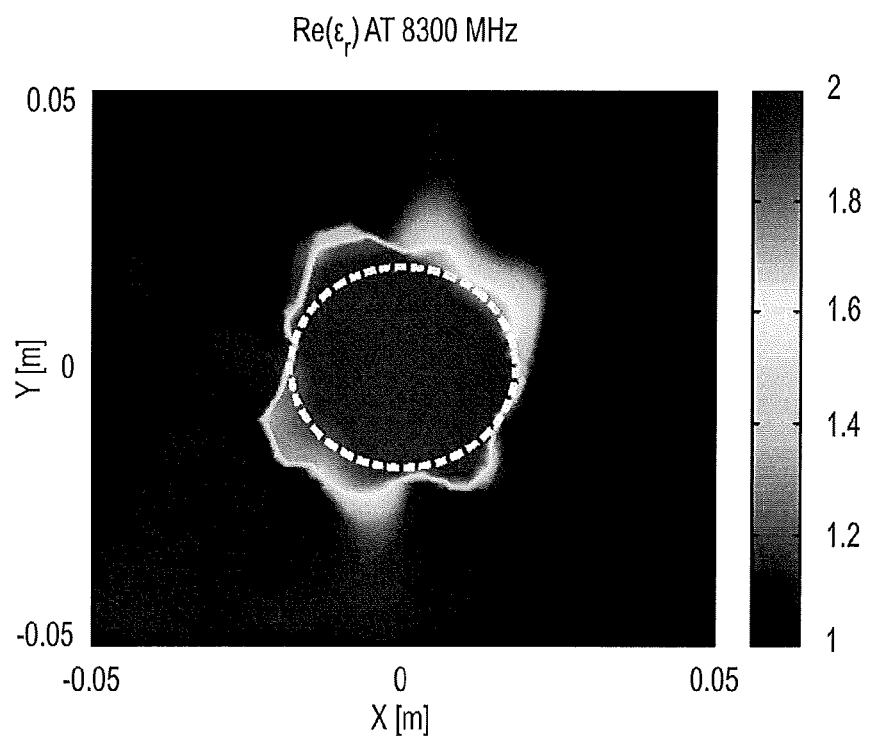
FIG. 16A is the real part of the dielectric permittivity of an exemplary reconstructed image of the object being imaged in FIG. 15.
Figure 16B:
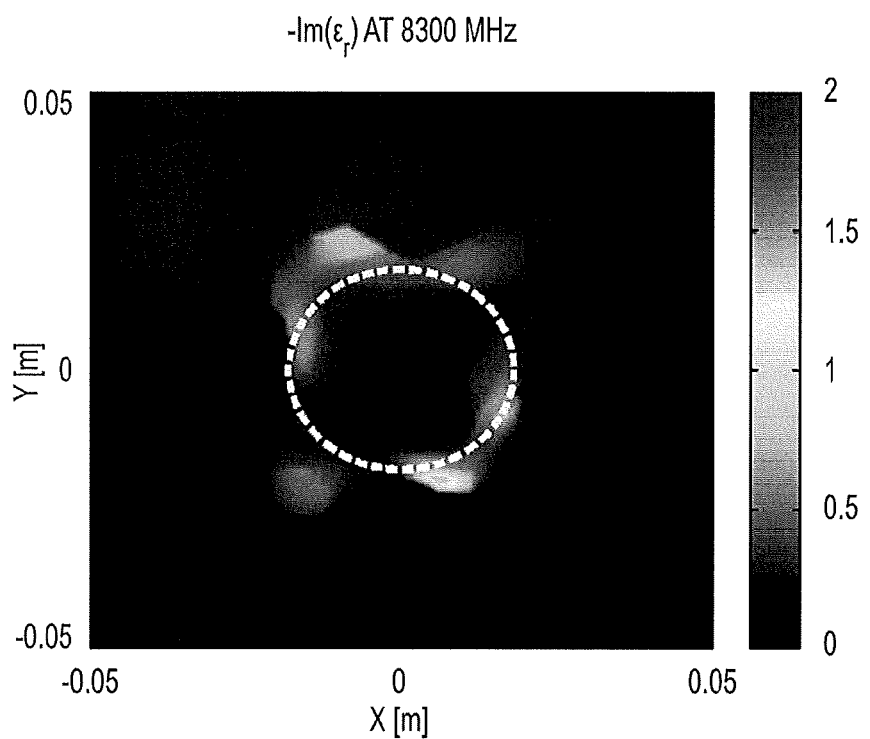
FIG. 16B is the imaginary part of the dielectric permittivity of an exemplary reconstructed image of the object being imaged in FIG. 15.
Figure 17A:
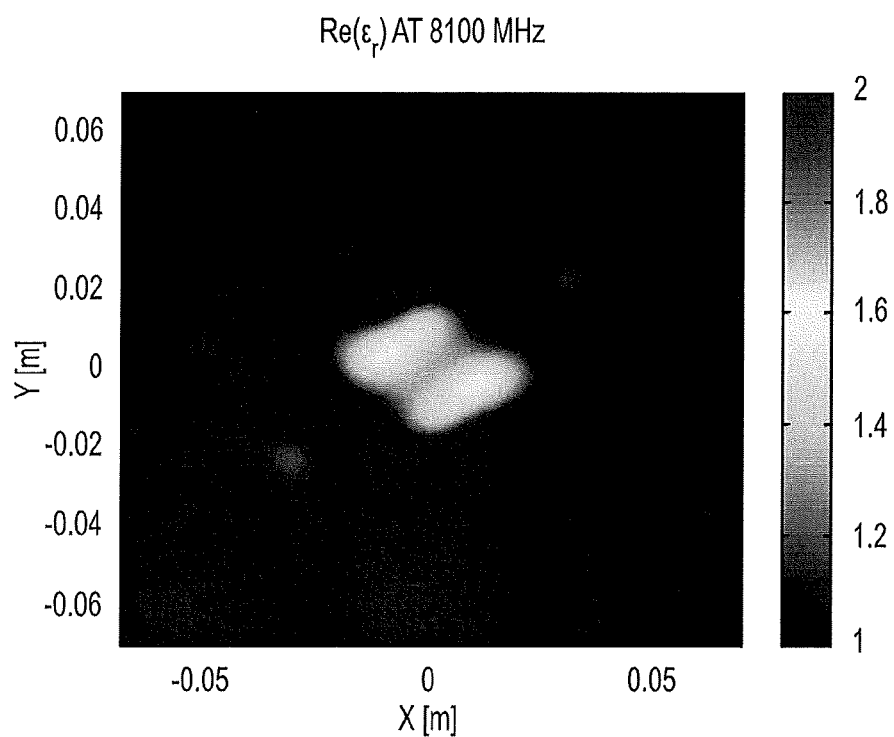
FIG. 17A is the real part of the dielectric permittivity of an exemplary reconstructed image of two wooden blocks imaged using the exemplary imaging setup of FIGS. 14-15.
Figure 17B:
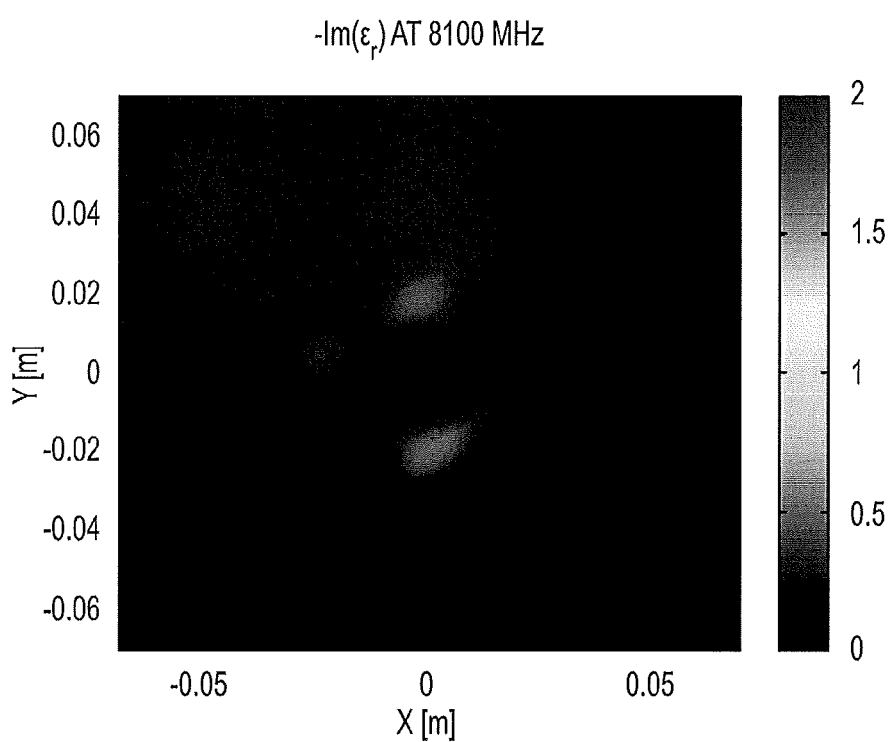
FIG. 17B is the imaginary part of the dielectric permittivity of an exemplary reconstructed image of two wooden blocks imaged using the exemplary imaging setup of FIGS. 14-15.

A first set of data was collected using a 1.5 inch diameter nylon rod 410 as shown in FIG. 15 and a second set of data was collected using two small wooden blocks, each 1×2 centimeters. The measured data were calibrated by a small metallic cylinder. The multiplicatively regularized CSI algorithm was utilized to invert the collected data. Imaging results of the nylon rod and wooden blocks are shown in FIGS. 16 and 17, respectively. Also, the collected dataset was limited to only 20 gated elements.

The exemplary systems and methods described herein may be able to better suppress noise and phase error, e.g., caused by, or due to, the stress on the cables, the RF multiplexer, and measurement instruments compared to many older MWI systems because, e.g., the cables/traces remain stationary during the modulated data collection and the effect of the cables/traces on the measurement is negligible. Also, the phase error due to different RF routings of the RF multiplexer vanishes. Thus, the exemplary systems and methods are not sensitive to cable length as well as the configuration of the RF multiplexer. Additionally, in the exemplary systems and methods, the gated elements not only collect the field but also illuminate the object. Due to the presence of the ground plane on the opposite side of the PCB, the biasing routings do not interfere with the data collection, nor make the numerical model sophisticated (e.g., because of being shielded by the 'ground' plane). Further, different polarizations may improve the image reconstruction either by providing higher resolution (e.g., TE polarization) or higher accuracy in image reconstruction (e.g., TM polarization) (see, e.g., M. Ostadrahimi, A. Zakaria, J. LoVetri, and L. Shafai, "A near-field dual polarized TE-TM microwave imaging system," Microwave Theory and Techniques, IEEE Transactions on, vol. 61, no. 3, pp. 1376-1384, 2013). Collecting and illuminating different polarizations such as vertical, horizontal, and slant polarizations may be useful using the exemplary systems and methods described herein.

The exemplary system can be accurately modeled by an image reconstruction algorithm due to the presence of the well-defined boundaries of the imaging chamber, which is the so-called ground plane of the PCBs. The waveguides can be rectangular, square, or cylindrical. Further, the waveguides can be open or enclosed. The location and polarization of the gated elements may change based on the excited modes of the waveguides. The waveguides can also be cascaded by means of transmission lines in different configurations such as meander line connection. Cascaded waveguides may eliminate the need for an RF switch/multiplexer and may simplify the data collection.

An adapter can be utilized in conjunction with the gated elements for utilizing different matching materials (e.g., different fluids). If adapters are used, gated elements and waveguides may not be redesigned for different matching materials.

As described herein, the PCB may define a fluid gate configured to allow a matching fluid to flow inside and outside of the waveguide assemblies. The fluid gate may be positioned at a spot with minimum interference with the data collection.

Figure 18B:
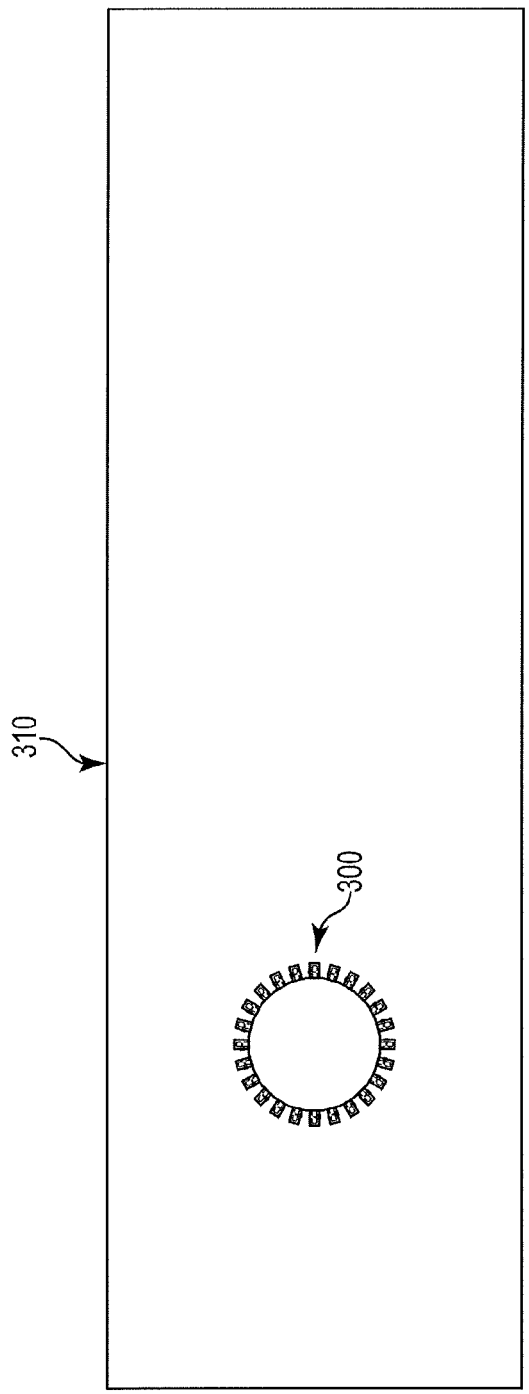
FIG. 18B is a top view of the system of FIG. 18A.

The exemplary systems and methods may be adapted for breast cancer screening in a configuration as shown in FIGS. 18A-18B. An imaging chamber 300 including a plurality of waveguide assemblies 302 may be attached, or coupled, to a bed structure 310. A woman may rest in prone position on the bed structure 310 while positioning one of her breasts into the imaging chamber 300. The chamber 300 can be filled with a matching fluid such as a water glycerin solution. The gated elements of the waveguide assemblies 302 may then illuminate the breast from different locations by using different polarizations while the remaining gated elements collect the scattered field as described herein. Once the data acquisition is completed, the data may be calibrated and processed for image reconstruction. The exemplary breast imaging technique can be either 2-D or 3-D and can be portable and used for chemotherapy treatment monitoring as well as a frequent breast cancer diagnostic.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A method of imaging an object using microwave imaging, wherein the method comprises:
    providing a plurality of waveguide assemblies positioned about an object, wherein each waveguide assembly of the plurality of waveguide assemblies comprises:
        a waveguide structure configured to deliver and sample electromagnetic energy, and
        one or more gated elements, wherein each gated element of the one or more gated elements defines an aperture extending into the waveguide structure, wherein each gated element of the one or more gated elements is configurable in at least a transmission state, a reception state, and a passive state, wherein each gated element of the one or more gated elements is configured to allow electromagnetic energy to radiate from the waveguide structure through the aperture when in the transmission state, to allow electromagnetic energy to be received through the aperture into the waveguide structure when in the reception state, and to neither allow electromagnetic energy to radiate from the waveguide structure through the aperture nor allow electromagnetic energy to pass through the aperture into the waveguide structure when in the passive state;
    delivering electromagnetic energy using at least one waveguide assembly of the plurality of waveguide assemblies to irradiate the object resulting in scattered electromagnetic energy;
    sampling the scattered electromagnetic energy using at least one waveguide assembly of the plurality of waveguide assemblies; and
    reconstructing an image of the object based on the sampled scattered electromagnetic energy.

2. The method of claim 1, wherein, to sample the scattered electromagnetic energy using at least one waveguide assembly of the plurality of waveguide assemblies, a modulation signal is applied to an individual gated element of the one or more gated elements to configure the individual gated element into the reception state.

3. The method of claim 2, wherein the modulation signal has a lower frequency than the electromagnetic energy delivered using at least one waveguide assembly of the plurality of waveguide assemblies.

4. The method of claim 1, wherein sampling the scattered electromagnetic energy using at least one waveguide assembly of the plurality of waveguide assemblies comprises sampling the scattered electromagnetic energy using each gated element individually of the one or more gated elements of each waveguide assembly of the plurality of waveguide assemblies until each gated element of the one or more gated elements of the plurality of waveguide assemblies has been individually used to sample the scattered electromagnetic energy, wherein, to sample the scattered electromagnetic energy using each gated element individually, a selected gated element is configured in the reception state, the remaining gated elements of the one or more gated elements of the plurality of waveguide assemblies are configured in the passive state, and the waveguide assembly comprising the selected gated element samples the scattered electromagnetic energy.

5. The method of claim 1, wherein delivering electromagnetic energy using at least one waveguide assembly of the plurality of waveguide assemblies comprises delivering the electromagnetic energy using each gated element individually of the one or more gated elements of each waveguide assembly of the plurality of waveguide assemblies until each gated element of the one or more gated elements of the plurality of waveguide assemblies has been individually used to deliver the electromagnetic energy, wherein, to deliver the electromagnetic energy using each gated element individually, a selected gated element is configured in the transmission state, the remaining gated elements of the one or more gated elements of the plurality of waveguide assemblies are configured in the passive state, and the waveguide assembly comprising the selected gated element delivers the electromagnetic energy to radiate from the selected gated element.

6. The method of claim 1, wherein the plurality of waveguide assemblies are in a fixed position relative to the object.

7. The method of claim 1, wherein the plurality of waveguide assemblies are positioned around a perimeter of the object to form at least a portion of an imaging chamber.

8. The method of claim 1, wherein the reconstructed image is a quantitative image.

9. The method of claim 1, wherein each waveguide assembly comprises two or more gated elements.

10. The method of claim 1, wherein each waveguide assembly is configured to provide a standing wave within the waveguide structure when electromagnetic energy is being delivered therefrom.

11. The method of claim 1, wherein the waveguide structure defines an enclosed volume for confining electromagnetic energy therein.

12. The method of claim 1, wherein each gated element of the one or more gated elements comprises a switchable segment configurable between a conducting configuration and a non-conducting configuration, wherein the switchable segment is configured in the conducting configuration when the gated element is in the passive state, and wherein the switchable segment is configured in the non-conducting configuration when the gated element is the transmission state.

13. The method of claim 1, wherein the aperture of each gated element defines a length that is half the wavelength of the electromagnetic energy delivered by the plurality of waveguide assemblies.

14. The method of claim 1, wherein the aperture of each gated element defines a slot, wherein the slot defines a width and a length perpendicular to the width, and wherein the length is greater than the width.

15. The method of claim 1, wherein the one or more gated elements comprise:
at least one gated element to collect electromagnetic energy of a first selected polarization when in the reception state; and
at least one gated element to collect electromagnetic energy of a second selected polarization when in the reception state, wherein the first selected polarization is different than the second selected polarization.

16. A system for use in imaging an object using microwave imaging, wherein the system comprises:
a plurality of waveguide assemblies positioned about an object, wherein each waveguide assembly of the plurality of waveguide assemblies comprises:
a waveguide structure configured to deliver and sample electromagnetic energy, and
one or more gated elements, wherein each gated element of the one or more gated elements defines an aperture extending into the waveguide structure, wherein each gated element of the one or more gated elements is configurable in at least a transmission state, a reception state, and a passive state, wherein each gated element of the one or more gated elements is configured to allow electromagnetic energy to radiate from the waveguide structure through the aperture when in the transmission state, to allow electromagnetic energy to be received through the aperture into the waveguide structure when in the reception state, and to neither allow electromagnetic energy to radiate from the waveguide structure through the aperture nor allow electromagnetic energy to pass through the aperture into the waveguide structure when in the passive state; and
processing apparatus coupled to the plurality of waveguide assemblies, wherein the processing apparatus is configured to:
deliver electromagnetic energy using at least one waveguide assembly of the plurality of waveguide assemblies to irradiate the object resulting in scattered electromagnetic energy;
sample the scattered electromagnetic energy using at least one waveguide assembly of the plurality of waveguide assemblies, and
reconstruct an image of the object based on the sampled scattered electromagnetic energy.

17. The system of 16, wherein, to sample the scattered electromagnetic energy using at least one waveguide assembly of the plurality of waveguide assemblies, a modulation signal is applied to an individual gated element of the one or more gated elements to configure the individual gated element into the reception state.

18. The system of claim 17, wherein the modulation signal has a lower frequency than the electromagnetic energy delivered using at least one waveguide assembly of the plurality of waveguide assemblies.

19. The system of 16, wherein sampling the scattered electromagnetic energy using at least one waveguide assembly of the plurality of waveguide assemblies comprises sampling the scattered electromagnetic energy using each gated element individually of the one or more gated elements of each waveguide assembly of the plurality of waveguide assemblies until each gated element of the one or more gated elements of the plurality of waveguide assemblies has been individually used to sample the scattered electromagnetic energy, wherein, to sample the scattered electromagnetic energy using each gated element individually, a selected gated element is configured in the reception state, the remaining gated elements of the one or more gated elements of the plurality of waveguide assemblies are configured in the passive state, and the waveguide assembly comprising the selected gated element samples the scattered electromagnetic energy.

20. The system of 16, wherein delivering electromagnetic energy using at least one waveguide assembly of the plurality of waveguide assemblies comprises delivering the electromagnetic energy using each gated element individually of the one or more gated elements of each waveguide assembly of the plurality of waveguide assemblies until each gated element of the one or more gated elements of the plurality of waveguide assemblies has been individually used to deliver the electromagnetic energy, wherein, to deliver the electromagnetic energy using each gated element individually, a selected gated element is configured in the transmission state, the remaining gated elements of the one or more gated elements of the plurality of waveguide assemblies are configured in the passive state, and the waveguide assembly comprising the selected gated element delivers the electromagnetic energy to radiate from the selected gated element.

21. The system of 16, wherein the plurality of waveguide assemblies are in a fixed position relative to the object.

22. The system of 16, wherein the plurality of waveguide assemblies are positioned around a perimeter of the object to form at least a portion of an imaging chamber.

23. The system of 16, wherein the reconstructed image is a quantitative image.

24. The system of 16, wherein each waveguide assembly comprises two or more gated elements.

25. The system of 16, wherein each waveguide assembly is configured to provide a standing wave within the waveguide structure when electromagnetic energy is being delivered therefrom.

26. The system of 16, wherein the waveguide structure defines an enclosed volume for confining electromagnetic energy therein.

27. The system of claim 16, wherein each gated element of the one or more gated elements comprises a switchable segment configurable between a conducting configuration and a non-conducting configuration, wherein the switchable segment is configured in the conducting configuration when the gated element is in the passive state, and wherein the switchable segment is configured in the non-conducting configuration when the gated element is the transmission state.

28. The system of claim 16, wherein the aperture of each gated element defines a length that is half the wavelength of the electromagnetic energy delivered by the plurality of waveguide assemblies.

29. The system of 16, wherein the one or more gated elements comprise:
    at least one gated element to collect electromagnetic energy of a first selected polarization when in the reception state; and
    at least one gated element to collect electromagnetic energy of a second selected polarization when in the reception state, wherein the first selected polarization is different than the second selected polarization.

30. The system of claim 16, wherein each waveguide assembly defines a fluid gate configured to allow matching fluid to flow into and out of the waveguide structure.

31. A waveguide assembly for use in microwave imaging comprising:
    a waveguide structure configured to deliver and sample electromagnetic energy; and
    one or more gated elements, wherein each gated element of the one or more gated elements defines an aperture extending into the waveguide structure, wherein each gated element of the one or more gated elements is configurable in at least a transmission state, a reception state, and a passive state, wherein each gated element of the one or more gated elements is configured to allow electromagnetic energy to radiate from the waveguide structure through the aperture when in the transmission state, to allow electromagnetic energy to be received through the aperture into the waveguide structure when in the reception state, and to neither allow electromagnetic energy to radiate from the waveguide structure through the aperture nor allow electromagnetic energy to pass through the aperture into the waveguide structure when in the passive state.

32. The assembly of claim 31, wherein each waveguide assembly comprises two or more gated elements.

33. The assembly of claim 31, wherein each waveguide assembly is configured to provide a standing wave within the waveguide structure when electromagnetic energy is being delivered therefrom.

34. The assembly of claim 33, wherein each waveguide assembly extends from a first end portion to a second end portion, wherein each of the first and the second end portion are configured for a shorting boundary condition to provide the standing wave.

35. The assembly of claim 31, wherein the waveguide structure defines an enclosed volume for confining electromagnetic energy therein.

36. The assembly of claim 35, wherein the waveguide structure comprises:
    a conductive wall portion extending around the enclosed volume and defining an opening; and
    a gated element portion positioned over the opening.

37. The assembly of claim 36, wherein the gated element portion comprises a printed circuit board.

38. The assembly of claim 36, wherein the gated element portion comprises a conductive layer conductively coupled to the at least one conductive wall portion.

39. The assembly of claim 36, wherein the gated element portion comprises a pair of electrical traces for each of the one or more gated elements, wherein the electrical traces are electrically shielded from the enclosed volume of the waveguide structure.

40. The assembly of claim 31, wherein each gated element of the one or more gated elements comprises a switchable segment configurable between a conducting configuration and a non-conducting configuration, wherein the switchable segment is configured in the conducting configuration when the gated element is in the passive state, and wherein the switchable segment is configured in the non-conducting configuration when the gated element is the transmission state.

41. The assembly of claim 31, wherein the aperture of each gated element defines a length that is half the wavelength of the electromagnetic energy delivered by the plurality of waveguide assemblies.

42. The assembly of claim 31, wherein the aperture of each gated element defines a slot, wherein the slot defines a width and a length perpendicular to the width, and wherein the length is greater than the width.

43. The assembly of claim 31, wherein the one or more gated elements comprise:
    at least one gated element to collect electromagnetic energy of a first selected polarization when in the reception state; and
    at least one gated element to collect electromagnetic energy of a second selected polarization when in the reception state, wherein the first selected polarization is different than the second selected polarization.

44. The assembly of claim 43, wherein the first selected polarization is perpendicular to the second selected polarization.

45. The assembly of claim 31, wherein each waveguide assembly defines a fluid gate configured to allow matching fluid to flow into and out of the waveguide structure.

* * * * *